United States Patent [19]
Akopov et al.

[11] 3,973,709
[45] Aug. 10, 1976

[54] SURGICAL INSTRUMENT FOR STITCHING ORGANS WITH THE AID OF METAL STAPLES

[76] Inventors: Ernest Mikhailovich Akopov, Dubninskaya ulitsa, 61, kv. 88; Petr Moiseevich Postolov, Sadovo-Triumfalnaya ulitsa, 4/10, kv. 105a, both of Moscow, U.S.S.R.

[22] Filed: Mar. 3, 1975

[21] Appl. No.: 554,691

[52] U.S. Cl. .............................. 227/19; 29/212 D; 128/334 R
[51] Int. Cl.² .................................... B31B 1/00
[58] Field of Search .......... 29/200 H, 212 R, 212 D, 29/270, 243.56; 128/334, 325, 337; 227/19

[56] References Cited
UNITED STATES PATENTS

| | | | |
|---|---|---|---|
| 3,144,654 | 8/1964 | Mallina et al. | 128/334 R |
| 3,601,302 | 8/1971 | Potekhina et al. | 227/19 X |
| 3,646,801 | 3/1972 | Caroli | 29/212 W X |
| 3,795,034 | 3/1974 | Strekopytov et al. | 29/212 D |
| 3,873,016 | 3/1975 | Fishbein | 227/19 X |
| 3,889,683 | 6/1975 | Kapitanov | 128/334 R X |

*Primary Examiner*—Victor A. DiPalma
*Attorney, Agent, or Firm*—Holman & Stern

[57] ABSTRACT

The proposed surgical instrument for stitching organs with the aid of metal staples in the "end-to-end," "end-to-side" and "side-to-side" methods, with the working part of the instrument disposed exteriorly of the organs being stitched, comprises two clamps each of the clamps having two jaws for clinching and fixing the organs being stitched and pivotally interconnected at one end so that, when joined together, the joint line of the jaws of each clamp is perpendicular to the joint line of the clamps. The clamp jaws mount magazines with slots for staples, staple pushers, dies with recesses for bending the staples, as well as a device for aligning the organs being stitched longitudinally with respect to the jaws, and a means for grasping the walls of the organs being stitched. The means for grasping the walls of the organs being stitched comprises cases with built-in toothed plates, said cases being mounted on each of the jaws in guides providing for a limited movability of each of said cases in a plane perpendicular to the joint line of the jaws and to the joint line of the clamps in such a manner that each of said cases may be set to either one of two extreme positions; with the cases set to one extreme position corresponding to the instant walls of the organs being stitched and clamped and grasped, the tips of the plate teeth are disposed between the butt surfaces of the clamp jaws and a certain distance in front of the butt surfaces of the clamps in their set-apart condition, while, with the cases set to the other extreme position corresponding to the instant of organ suturing with the clamps being joined, the tips of the plate teeth lie a certain distance from the butt surfaces of the clamp jaws and approximately in the planes of the butt surfaces of the clamps.

27 Claims, 48 Drawing Figures

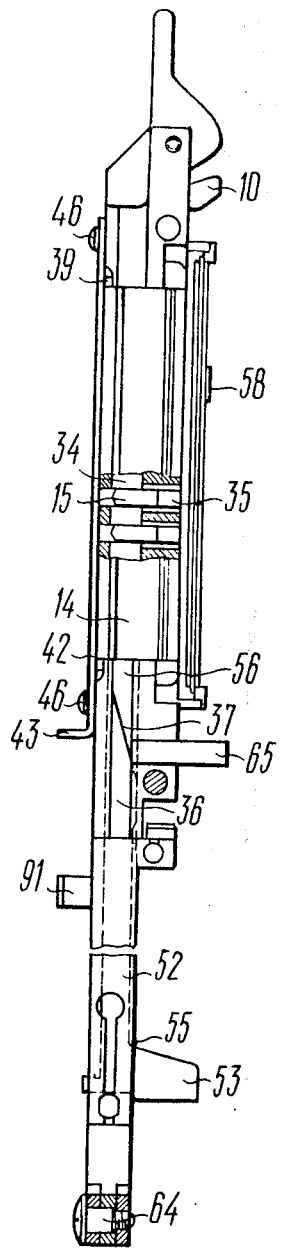
FIG.11
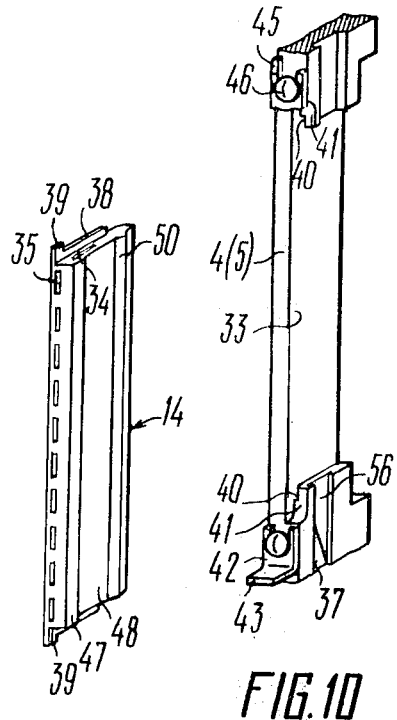
FIG.9
FIG.10
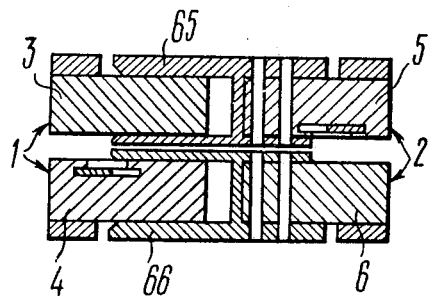
FIG.13

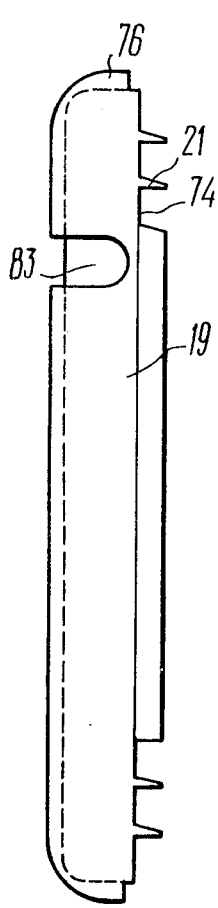
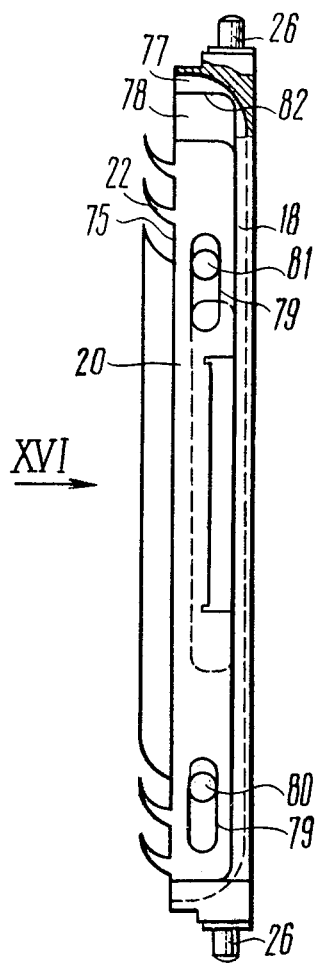
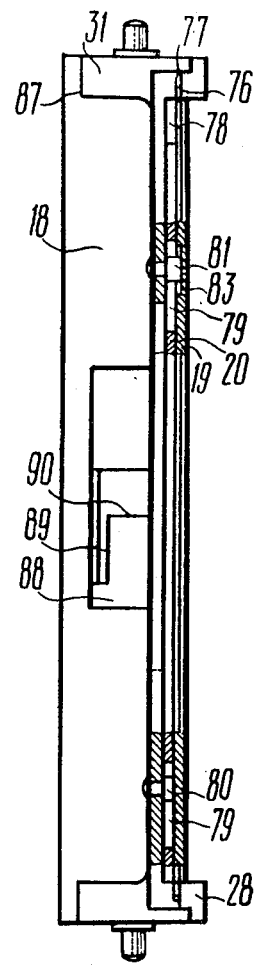
FIG.14   FIG.15   FIG.16
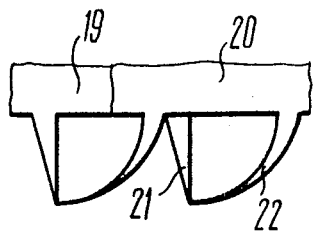
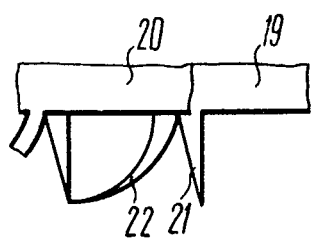
FIG.17   FIG.18

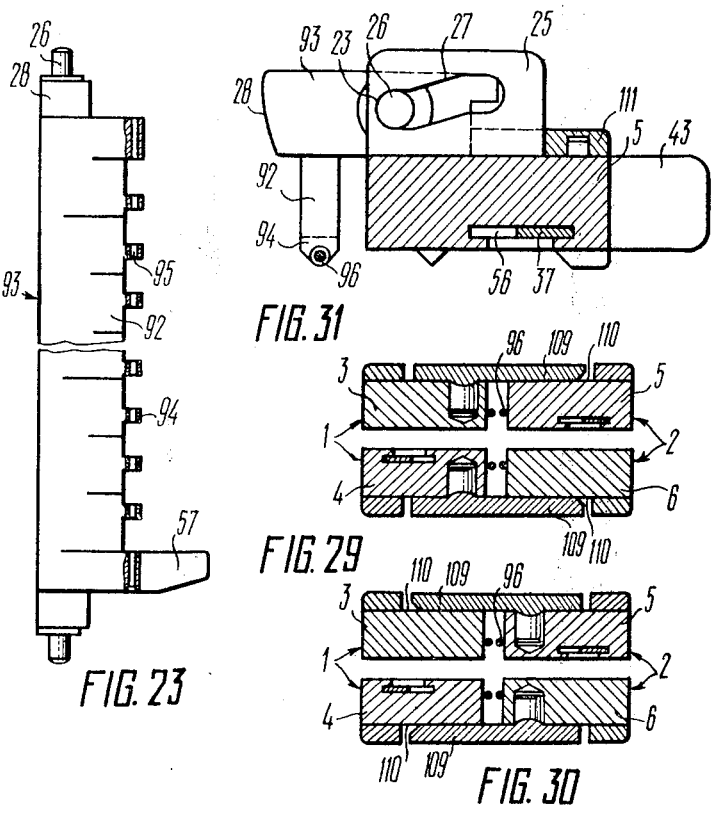

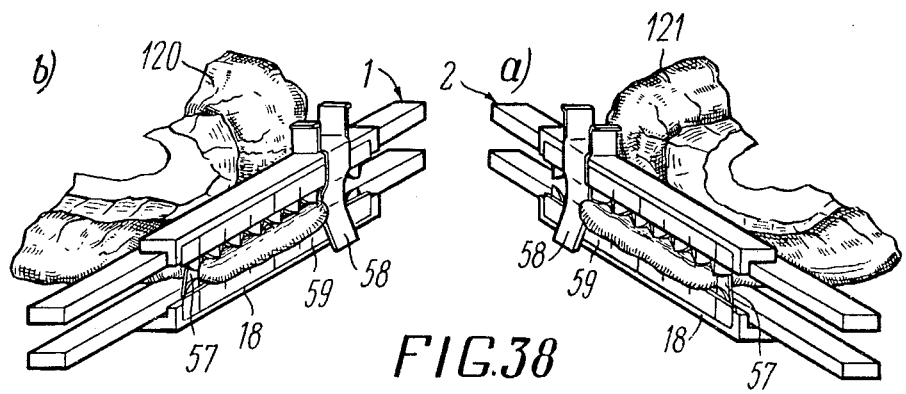
FIG.38
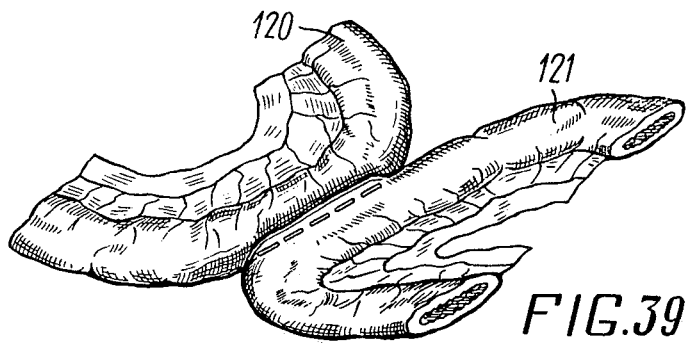
FIG.39
FIG.25
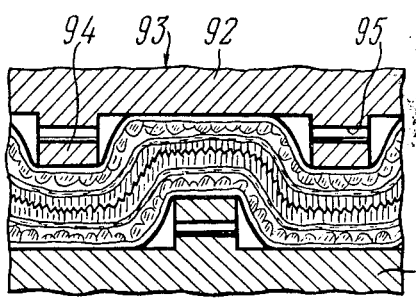
FIG.26
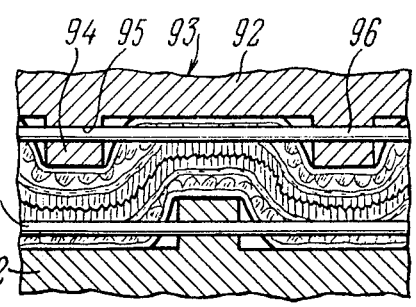

SURGICAL INSTRUMENT FOR STITCHING ORGANS WITH THE AID OF METAL STAPLES

BACKGROUND OF THE INVENTION

The present invention relates to medical equipment, and, more particularly, to surgical instruments for stitching organs with the aid of metal staples. The proposed instrument is designed for stitching both hollow organs and solid organs and tissues in the end-to-end, end-to-side and side-to-side methods, with the working part of the instrument being disposed exteriorly of the organs being stitched.

The proposed instrument may be employed, inter alia, for applying anastomoses onto digestive canal organs, for instance, intestinal anastomoses.

It is known in the art to employ an instrument for stitching organs with the aid of metal staples in the end-to-end, end-to-side and side-to-side methods, with the working part of the instrument disposed exteriorly of the organs being stitched, which is designed for applying intestinal anastomoses.

This known instrument incorporates two interconnected clamps, each of the clamps having two jaws for clinching and fixing the organs to be stitched. The clamps are pivotally interconnected at one of their ends, the joint line of the jaws of each of the clamps being perpendicular to the joint line of the clamps. In the closed condition of the clamps, the butt surfaces of the clamps adjoin each other, i.e. the clamps are so interconnected that there is no clearance between the aligned paired jaws of different clamps.

The clamp jaws mount a means for grasping and fixing the walls of the organs to be stitched with toothed plates, magazines with slots for staples and pushers for forcing the staples out of the magazines, dies for bending the staples, as well as a device for aligning the organs to be stitched longitudinally with respect to the jaws.

The means for grasping the walls of the organs to be stitched provided in the known instrument comprises two draw-out toothed plates mounted in recesses provided in each jaw of the clamps, a cover for fastening the toothed plates to the jaws, and a drive means disposed in said jaw recess and serving to draw the toothed plates out of the jaws and to displace the toothed plates one relative to the other.

The toothed plates adjoin each other by way of the lateral surfaces thereof and in their initial position are fully recessed in the clamp jaws. The teeth of the plates are formed as cooperating pairs of fixing needles spaced at equal intervals along the longitudinal edges of the plates and curved in such a manner that the tips of the needles, or claws, of one plate are directed towards the tips of the claws of the other plate.

The plates with the claws have inclined slots of equal length formed therein, and the inclined slots of one of the plates terminate in longitudinal slots whose length corresponds to the distance between the tips of the paired curved claws in their initial position. The length of the plate with the inclined and longitudinal slots is equal to the length of the recess formed in the jaw, and this plate can move laterally with respect to the jaw.

The length of the plate having only inclined slots is smaller than that of the recess, and this latter plate can move both laterally and longitudinally with respect to the jaw. The drive of the plates with the fixing claws is provided with projections entering the slots of both plates, as well as with a handle for manipulating said drive.

The drive, and accordingly the projections thereof, occupies either one of two extreme positions relative to the plates with the claws; with the drive set to one, initial, extreme position, the tips of the paired curved claws are set apart and recessed in the clamp jaw, whereas, with the drive set to the other position, the tips of the claws are joined and project from the jaw towards the joint line of the clamp jaws.

With the drive of the plates set to the latter position, the jointed claws grasp and fix the walls of the organ to be stitched.

In the known instrument, the working part of the clamp jaws which carries the means for grasping the walls of the organs to be stitched, as well as the magazines and the dies is formed as part of a cylinder. A magazine is slidably mounted in cylindrical guides on the cylindrical surface of one jaw of each clamp, whereas on the cylindrical surface of the other jaw of the clamp there is mounted a die, which magazine and die cooperate, while stitching organs and after the clamps have been closed, with the die and magazine, respectively, mounted on the paired jaws of the other clamp. The magazines and dies are able to rotate about the jaws of the clamps to be set to either one of two extreme positions. In one extreme position, viz. the working position, the magazine and the die of the jaws of the joined clamps are aligned for stitching and disposed between the butt surfaces of the clamp jaws. In the working position, the butt surfaces of the aligned and coacting magazines and dies are disposed in parallel relationship at a certain distance corresponding to the mean of the possible thicknesses of the tissues being stitched, the slots for the staples of the magazine and the recesses for bending the staples of the dies being directed towards one another.

In the other, initial, position, the cooperating magazine and die are withdrawn from the zone between the butt surfaces of the clamp jaws, and the butt surfaces of the magazine and the die are in angular relationship.

The magazine and the die of the paired jaws of the clamps are transferred from their initial position to the working position with the aid of revolving cams disposed on the jaws of one of the clamps and, after the clamps have been joined, acting on the projections rigidly coupled with the magazine and the die.

The design features of the known instrument provide for the following characteristic arrangements of the functional members of the instrument corresponding to the various characteristic stages of surgical procedure.

As the organs to be stitched are gripped between the jaws of the clamps, the plates with the fixing claws are fully recessed in the clamp jaws, the paired fixing claws are set apart, and the magazine and the die set to their initial position are fully withdrawn from the zone between the butt surfaces of the clamp jaws.

As the walls of the organs being stitched are fixed, the fixing claws of the plates of the means for grasping and fixing the organ walls project beyond the butt surfaces of the clamp jaws and are disposed in the zone between these surfaces, the paired fixing claws being closed. The magazine and the die of the clamp are in their initial position.

While stitching one of the semiperimeters of the aligned walls of the organs, the clamps are joined together, and the joined paired jaws of the clamps are set a certain distance apart. The aligned magazine and die of one pair of the clamp jaws, which is used to stitch the wall semiperimeter, are disposed in their working position between the butt surfaces of the somewhat set-apart paired jaws of the clamps and between the tips of the fixing claws of the clamp jaws, the distance between the magazine and the die being far smaller than the distance between the fixing claws of this joined pair of jaws of different clamps. The magazine and the die of the second pair of jaws of the clamps are disposed in their initial position.

The magazine of the known instrument is formed as a case of intricate spatial configuration with an interior cylindrical surface rotating with respect to the cylindrical surface of the clamp jaw. The case is provided with slots for the staples whereinto sectional pushers are fitted. As the surgeon's fingers manipulate each section of the pushers, 3 to 4 staples are simultaneously forced out of the magazine. The base of the pusher section in the initial position protrudes beyond the magazine, so that, to prevent accidental movement of the pushers and accidental forcing of the staples out of the magazine, the latter is provided with a guard lock which fixes the pushers in the initial position. To enable stitching, the guard lock must be disengaged from the pushers. Just as the drive of the plates with the fixing claws of the means for grasping the walls of the organs to be stitched, the pusher guard lock is formed as plates with a bent end serving as a handle. The handles of the guard lock and of the drive-similar in design and appearance, are disposed on the clamp jaws next to each other.

The die of the known instrument, just as the magazine, has an interior cylindrical surface and is so connected with the clamp jaw as to be able to execute a rotary motion with respect to the cylindrical surface of the jaw.

The magazine and the die of each clamp are provided with cam projections rigidly coupled therewith. These cam projections are designed for setting the clamp jaws apart as the magazine or the die secured to one of the clamp jaws is turned into its working position.

While this turn is being executed, the cam projections come to rest against the surface of the second clamp jaw, driving the jaws apart.

The magazines and the dies are provided with no rotary movement limiter as far as the jaws are concerned; hence, they can be freely removed from their cylindrical guides.

To ensure accurate alignment of the magazines and the dies during stitching, the butt surfaces of one of the clamps are provided with blind holes in the middle portion of the jaws, which blind holes cooperate with pins rigidly secured to the butt surfaces of the other clamp, fixing the paired clamp jaws in a closed condition.

The known instrument is manipulated in the same way whether employed for stitching organs in the end-to-end, side-to-side or end-to-side methods, for which reason its operation will be described only for the case of end-to-end stitching.

Prior to operation, the plates with the fixing claws of the means for grasping and fixing the walls of the organs to be stitched, as well as the magazines and the dies of the clamps must be set to the initial position, and the pushers must be immobilized in the initial position with the aid of the guard lock.

One of the organ ends having the largest semiperimeter is gripped between the jaws of one of the clamps within the limits of the scale of the device for the alignment of the organs being stitched in a longitudinal direction relative to the jaws. Moving the handles of the drives of the plates with the fixing claws of the means for grasping and fixing the walls of the organs being stitched, the drive projections are brought to bear on the slots of the plates with the fixing needles, driving them clear out of the clamp jaws and displacing them one relative to the other. While this operation is being effected, the tips of the paired claws transfix the walls of the organs and then move to meet one another, grasping the tissues in nodes. The organ part to be excised is cut off along the jaws of the former clamp.

Corresponding to the position of the organ gripped and fixed by the jaws of the first clamp by its scale, the second end or the organ to be stitched is positioned between the jaws of the second clamp by its scale. If its semiperimeter is less in cross section than that of the first end being stitched, it is so turned between the jaws of the clamp that the edges of the semiperimeter at the point where the organ is grasped lie precisely between the graduation notches on the scale corresponding to the position of the semiperimeter of the first end of the grasped organ relative to the graduation notches on the scale of the first clamp. After the walls of the second end of the organ being stitched have been fixed in a procedure identical to that used for the first end, the part of the organ that is to be excised is cut off.

Then the two clamps are brought together and fixed so that the butt surfaces of the clamps are in contact, and the sections of the semiperimeters of the clamped and fixed organ ends come to be mutually aligned.

By turning the rotary cams through 90°, the magazine and the die of one pair of joined clamp jaws are transferred from the initial position to the working position. The cam projections of the magazine and the dies cooperate in the process with the surfaces of the second pair of clamp jaws to set the pairs of joined jaws a certain distance apart. At this instant, the fixing claws immobilize the edges of the walls of the aligned organs relative to the set-apart paired jaws, and the magazine and the die turn, acting on the outer walls of the organs being stitched which are disposed, relative to the fixing claws, on the side opposite to the clamp joint line, and bringing into contact the inner surfaces of the walls of the organs being stitched.

With the magazine and the die set to their working position, one semiperimeter of the walls of the organs being stitched can be sutured. In this position, each edge of the walls being stitched is bent as an S-shaped loop.

In order to effect the stitching the surgeon manipulates the sectional pusher guard lock handle to disengage it from the pushers, thus setting them free. Pressing with his fingers on each pusher section in succession, the surgeon forces the staples from the magazine and stitches one semiperimeter of the walls of the organs being stitched. This stitching stage over, the cam is turned at 90° to be returned to the initial position, after which the magazine and die projections are rotated about the joined jaws to return the magazine and the die to their initial position.

In order to stitch the second semiperimeter of the intestinal walls, the cam of the second pair of joined jaws disposed beneath the organs being stitched is turned at 90°, after which all of the manipulations used in the suturing of the first semiperimeter of the walls being stitched are repeated.

Having stitched both semiperimeters of the organ walls, the drives of the means for grasping the organ walls are reset, the paired fixing claws being first set apart and recessed in the appropriate depressions formed in the clamp jaws. The locking hooks coupling the jaws of the joined clamps are turned and the upper pairs of clamp jaws are drawn away from the lower pairs of clamp jaws disposed beneath the sutured ends of the intestine in the space between the mesenteries of both stitched parts, after which the lower pairs of jaws are withdrawn from beneath the stitched intestine.

The organ stitching operation by use of the prior art instrument involves about 30 strictly sequenced manipulations, with any violation of the operation sequence resulting in a faulty anastomosis.

While stitching organs in the end-to-side method by use of the prior art instrument, first the end of one of the organs to be stitched is clinched and fixed between the jaws of one of the clamps, after which the side of the other organ to be stitched is clinched and fixed between the jaws of the other clamp in accordance with the size and position of said organ end as indicated on the scales of the device for mutually aligning the organs to be stitched in a longitudinal direction with respect to the jaws.

When stitching organs in the side-to-side method by use of the prior art instrument, the side portions of the organs to be stitched are clinched by the scales of both clamps and fixed in such a way that their position with respect to the paired clamp jaws being aligned exactly matches the size of the side anastomosis preset by the surgeon.

Barring the foregoing specific features, the instrument is handled while stitching organs in the end-to-side and side-to-side methods actually in the same way as while applying anastomoses in the end-to-end method.

The principal disadvantage of the prior art surgical instrument for stitching organs with the aid of metal staples consists in that the toothed plates of the means for grasping and fixing the walls of the organs being stitched are built into the clamp jaws, are made on the draw-out principle and secured with the aid of covers; the claws of the plates are positioned, in the course of stitching, between the butt surfaces of the clamp jaws, on the one hand, and the rotatable magazines and dies set to their working position, on the other; and the distance between the claws of the plates of the joined pairs of clamp jaws largely exceeds the stitching clearance between the butt surfaces of the magazine and the die joined for stitching.

Owing to this, the plate claws are disposed a considerable distance from the staple suture applied and hence twist the fixed walls of the organs being stitched in an S-shaped loop, resulting in a sizeable lip (the distance from the suture line to the organ wall section) of the anastomosis when stitching hollow organs. This condition hampers tissue regeneration and gives rise to a large bead at the point of organ union after the second row of the suture is applied while stitching the digestive canal organs, the second row of the suture being applied manually.

The foregoing disadvantage is prohibitive to stitching solid organs.

Furthermore, the prior art instrument lacks operating reliability, entailing a high risk of leaving unstitched organ portions or placing poor-quality sutures.

Thus, in particular, the magazines and the dies rotating about the cylindrical guides of the jaws are unreliably fixed in the working position with the aid of the rotary cams, with the result that in the course of stitching the butt surfaces of the magazine and the die are disengaged one from the other and assume an angular relationship, and the tips of the staples being ejected from the magazines fail to enter the respective recesses formed in the dies.

As a result, the U-shaped staples transfix the walls of the organs but fail to stitch them.

Equally unreliable are the sectional pushers manipulated directly by the surgeon's fingers. Owing to the large overall deforming force of several staples, as well as to the possible jamming and sticking of the sectional pushers, the staples may fail to emerge clear of the magazine, resulting in poor connection of the walls of the organs being stitched, lack of tissue haemostasis and suture tightness.

Sometimes the prior art instrument cannot be taken off the sutured organs without additionally injuring them. The grasping of the organ walls after stitching while withdrawing the instrument from the surgery wound is due to the fact that the claws of the plates of the means for grasping the organ walls are formed as curved members directed towards one another. After stitching and disengagement of the claws of one plate from those of the other plate, the claws are retracted into the narrow recess formed in the clamp jaws, drawing in the tissues they cling to. The danger of the disengaged claws gripping tissues is all the more real since the claws of one of the plates point in the direction of withdrawal of the instrument from the surgery wound.

The prior art instrument is difficult to handle and surgeons have to spend a lot of time and effort to master it, for the stitching operation involves as many as about 30 manipulations sequenced in a definite order. Violation of this sequence and possible instrument handling mistakes due to the design drawbacks result in non-stitching incidents or poor-quality sutures. Thus, the design of the prior art instrument allows the clamps to be joined and the rotary magazines and dies to be set to the stitching position while the organ walls are still unfixed, so that all of the subsequent stitching manipulations result in a defective suture, violation of the sterility requirements and, hence, attempts to repeat the stitching operation.

The operation may become septic and the suture may be defective also due to the fact that in the prior art instrument the handle of the pusher guard lock, preventing accidental forcing of the staples out of the magazine, and the handle of the drive of the toothed plates of the means for grasping and fixing the walls of the organs being stitched are disposed side by side, being similar in design and shape. Consequently, after the magazine and the die have been set to their working position for stitching the semiperimeter of the organ walls, the surgeon is liable to confuse the handles and, instead of manipulating the handle of the pusher guard lock, to mistakenly actuate the handle of the drives of the plates of the means for fixing the organ walls, releasing the latter, with the result that the aligned edges of the organ walls will slip from the zone between the magazine and the die.

The clamp jaws of the prior art instrument have a large cross-section attributable to the draw-out design of the plates of the means for grasping and fixing the walls of the organs being stitched, as well as to the use of awkward rotary magazines and dies rotating about the cylindrical surface of the clamp jaws. In consequence of this, the prior art instrument is functionally limited in use; thus, it can hardly be employed, for instance, for stitching intestines having a short mesentery.

Another disadvantage of the prior art instrument consists in that it is impossible to achieve an optimal alignment of the layers of the walls of the organs being stitched under varying conditions of surgery, such as the thickness of the walls of the organs being stitched, the state of the organ walls, and the like.

Besides, there are some further disadvantages inherent to the prior art instrument which impose limitations on its use. They are as follows:

since the magazines and dies are insecurely fixed in the initial position, they are likely to fall out of the cylindrical guides while the instrument is being manipulated;

the pushers of the magazines which at the instant of stitching are positioned beneath the organs being stitched are hardly accessible;

it is impossible to apply several anastomoses during an operation without recharging the magazines with staples;

the rotatable magazines and dies are likely to be incorrectly fitted into the guides of the clamp jaws while assembling the instrument, rendering the instrument unusable; and the fixing toothed plates are likely to be misplaced in the clamp jaws so that the coacting claws of the plates are not directed towards one another, making it impossible to fix the tissues.

The device for mutually aligning the organs to be stitched lengthwise relative to the clamp jaws fails to ensure an adequate accuracy of the alignment of the organ portions being stitched in a longitudinal direction, so that some organ portions remain unstitched. Also, the need to position and clinch the organ portions to be stitched between the clamp jaws by the scales proves a hindrance, since the surgeon has to simultaneously align two edges of the semiperimeters of the organ portions to be stitched, watching both scales.

It is likewise inconvenient to fix the paired jaws of the clamps with the aid of blind holes cooperating with pins, for the blind holes accumulate dirt and are difficult to maintain clean.

The design of the prior art instrument being so sophisticated, it is awkward and heavy and hence difficult to manipulate in the surgery wound. And finally, the prior art instrument is difficult to manufacture.

Summary of the Invention

It is an object of the present invention to provide a surgical instrument for stitching organs with the aid of metal staples in the end-to-end, end-to-side and side-to-side methods, with the working part of the instrument being disposed exteriorly of the organs being stitched, which ensures a higher quality of the sutures placed by substantially decreasing the distance from the tissue section to the sutures.

It is another object of the present invention to provide a surgical instrument which is easy to handle and requires fewer manipulations for placing sutures, thus practically eliminating any possibility of erroneous handling of the instrument and hence actually obviating any possibility of obtaining poor-quality sutures because of mishandling.

It is a further object of the invention to improve the reliability of the instrument, make it impossible to detach the instrument from the sutured organs in an accidental way, enable the clamp jaws to be withdrawn from beneath the sutured organs without injuring same, make it impossible to close the clamps for stitching with the organs unfixed, and provide for a trouble-free and stable operation of the instrument components.

It is still another object of the invention to extend the functional range of the instrument by enabling both hollow and solid organs and tissues to be stitched therewith, as well as by providing for the possibility of stitching organs and tissues with a limited operation space therebeneath, e.g. intestines with a shorter mesentery that can be handled by the prior art instrument, through reducing the cross section of the working part of the clamp jaws of the instrument.

It is yet another object of the invention to provide for a higher accuracy of alignment of the organ portions being stitched lengthwise relative to the clamp jaws, thereby minimizing the possibility of leaving some sections of the organs unstitched, as well as to simplify the process of placing and clinching the organs to be stitched between the clamp jaws.

One more object of the invention is to provide for atraumatic clamping of the organs to be stitched between the clamp jaws if their thickness varies over a wide range, thereby minimizing the inflammatory process in the vicinity of the sutures placed with the aid of the instrument.

Still another object of the invention is to provide for the possibility of adjusting the arrangement of the wall layers of the organs being stitched.

Also, an object of the invention is to simplify the design of the instrument, to provide simpler assembling and disassembling procedures, improved maintenance and cleaning procedures, and to make the instrument easier to manufacture.

The foregoing objects are attained in a surgical instrument for stitching organs with the aid of metal staples in the end-to-end, end-to-side and side-to-side methods, with the working part of the instrument being disposed exteriorly of the organs being stitched, which comprises two clamps, each of the clamps incorporating two jaws for clinching and fixing the organs being stitched and pivotally interconnected so that, with the clamps being closed, the joint line of the jaws of each clamp is perpendicular to the joint line of the clamps, a means mounted on the clamp jaws and serving for grasping and fixing the walls of the organs to be stitched incorporating toothed plates disposed along the jaws, magazines with slots for the staples, staple pushers and dies with recesses for bending the staples, all of the members being mounted on the clamp jaws, and the magazines and the dies which cooperate at the instant of placing sutures being disposed on the jaws belonging to different clamps, as well as a jaw-mounted device for aligning the organs to be stitched in a longitudinal direction with respect to the jaws, in accordance with the invention, the means for grasping the walls of the organs to be stitched is formed as cases whereinto said toothed plates are built, and said cases are mounted on each of the jaws in guides providing for a limited movability of each of said cases in a plane perpendicular to the joint line of the clamp jaws and to the joint line of the clamps so that each of said cases may be set to either one of two extreme positions in one of which, a forward position corresponding to the instant of clinching and grasping the walls of the organs to be stitched, the tips of the teeth of the toothed plate are disposed between the butt surfaces of the clamp jaws and a certain distance in front of the butt surfaces of the clamps in their set-apart condition, whereas in the other position, a backward position corresponding to the instant of placing sutures with the clamps being closed, the tips of the teeth of the toothed plates are disposed a certain distance from the butt surfaces of the clamp jaws and approximately in the planes of the butt surfaces of the clamps.

The guides are preferably formed as closed through slots having inclined portions in each of the jaws which cooperate with pins so secured on the cases that as said cases move from one extreme position to the other they are simultaneously turned in a plane perpendicular to the butt surfaces of the jaws of each clamp and to the butt surfaces of the clamps.

It is desirable that each of the cases be provided with cam projections cooperating with respective similar cam projections on the cases of the opposite clamp so that as the clamps are closed to the position for placing sutures, the cases are simultaneously transferred from their forward positions to their backward positions.

The shape and layout of the cam projections on the cases are preferably so selected that at each instant of interaction of the cam projections of the opposite cases while the clamps are being closed, the forces exerted on the cases are directed eccentrically with respect to the pin axes so that the cases being transferred from the forward to the backward positions may be simultaneously turned in a desired direction.

The magazines may be formed to have longitudinal through slots perpendicular to the slots for the staples, and the staple pushers may be provided with drives formed as plates secured to the jaws so as to be able to execute a lengthwise motion within said through slots of the magazines, the front edge of said plates having wedge-shaped chamfers cooperating with the pushers for forcing the staples out of the magazine.

The magazines may be provided with transversely arranged external projections with stops, whereas the jaws carrying the magazines may be formed to have transverse depressions cooperating with said projections and thereby enabling the magazine to be installed and removed, and the jaws may be further provided with fixing plates pressing the magazines against the jaws.

The pusher drives may be provided with handles having springy sections, and the jaws may be provided with projections cooperating with said springy sections and serving as means for locking the pusher drives in their initial position.

The pusher drives are preferably fastened to the jaws by means of detachable plates.

The clamps are desirably interconnected at one end with a split hinge latch and provided at the other end with means for fixing the clamps relative to each other with a required clearance therebetween.

The device for aligning the organs to be stitched lengthwise relative to the jaws desirably comprises stationary stops delimiting the edges of the semiperimeters of the organs being stitched as the latter are clamped between the jaws on one side, and movable stops delimiting the edges of the semiperimeters of the organs being stitched on the other side, of the stops being secured to one of the jaws of each clamp and disposed one opposite another.

The movable stops may be made detachable.

The stationary and movable stops may be secured to the cases of the means for grasping and fixing the walls of the organs to be stitched, and the cases may be provided with graduated scales facilitating the task of positioning of the movable stops.

Each of the clamps is desirably provided with a lock arrangement for fixing the clearance between the jaws while clinching the organ being stitched, which arrangement comprises an irregularly shaped lath spring secured at one end to one of the jaws of the clamp as well as stepped recesses formed in the other jaw and cooperating with the other end of the spring, the particular recess cooperting with the spring depending on the wall thickness of the organ being clinched.

In this case the spring may protrude beyond jaw with the stepped recesses, and each of the clamps may be provided with a handle disposed on this jaw next to the protruding end of the spring in such a way that, with the handle and the spring pressed together, the spring comes out of engagement with the stepped recess.

Each case of the means for grasping and fixing the walls of the organs being stitched may comprise two toothed plates adjoining each other by way of the lateral surfaces thereof, and the plate teeth may be formed as fixing needles disposed at equal intervals on the surfaces of the longitudinal edges of both plates, the fixing needles of one of the plates being straight and roughly perpendicular to the longitudinal edge of the plate, while the fixing needles of the other plate being curved in one direction opposite to the supposed direction of withdrawal of the instrument from the surgery wound and adjoining by way of their tips the tips of the straight fixing needles, defining closed contours, and one of the plates is fixed on the case for grasping and fixing the walls of the organs being stitched, while the other plate is so mounted on the case for grasping the fixing the walls of the organs being stitched as to be able to slide along the stationary plate.

The toothed plates are desirably so mounted on the cases that they can be replaced.

Each of the jaws may be equipped with a locking device for preventing organ stitching if the organ walls are unfixed, which at the same time functions as a drive of the movable plate, said device being formed as a plate disposed along the appropriate jaw and able to move lengthwise, and said plate being provided with a dog cooperating with the movable plate with the fixing needles as well as with stops cooperating with the movable cases which in their forward position protrude the plane of the butt surfaces of the clamps a distance exceeding half the clearance between the butt surfaces of the joined clamps so that, with the plate being in one of its extreme positions corresponding to the initial position of the movable plate with the fixing needles prior to grasping the walls of the organ to be stitched, the plate stops cooperate with the case, preventing its transfer to the backward position and the closing of the clamps for placing sutures, whereas with the plate being in the other extreme position, the movable plate is set to the position for grasping the walls of the organ to be stitched with its fixing needles, while the plate stops are disengaged from the case, enabling the case to be drawn to its extreme backward position and thereby making it possible to close the clamps and effect the suturing operation.

The toothed plates may likewise be fixed on the cases of the means for grasping the walls of the organ being stitched, the plate teeth may be formed to have coaxial through holes and each of the cases may be provided with a needle run through said through holes and through the walls of the organ being sutured as it is gripped between the jaws.

Each of the clamps is preferably provided with a lock means for fixing the clearance between the jaws as the ends of the organ being stitched are clinched, which lock means is formed as spring catches disposed on the ends of the jaws.

The jaws may be interconnected by means of two forks rigidly fastened to the mid-portion of the jaws of one clamp and enveloping with their prongs the jaws of the other clamp.

As compared with the prior art instrument, the proposed surgical instrument for stitching organs with the aid of metal staples in the end-to-end, end-to-side and side-to-side methods with the working part of the instrument being disposed exteriorly of the organs being stitched, permits placing higher-quality sutures, has a wider functional range, is far more reliable in handling, more convenient in maintenance, simpler in design and easier to manufacture; it also provides for a higher speed of stitching. The instrument in accordance with the present invention is fairly simple in handling in spite of the fact that it is called upon to perform a wide range of complex functions and meets a long list of medical and technical requirements. Thus, when used for stitching hollow organs of the digestive canal, e.g. for applying intestinal anastomoses, it ensures a high level of sterility, tight contact of the intestinal walls sutured together including the mucous membranes, high suture tightness and the required tissue haemostasis, strict adaptation of the analogous layers of the sutured walls, and minimal traumatization of the anastomosis edges in the course of suturing, which avoids necrosis of the tissue edges.

The proposed surgical instrument for stitching organs with the aid of metal staples used for stitching hollow organs permits reducing by a factor of 2 to 2.5 the distance from the tissue section to the sutures and aligning the walls of the organs being stitched in an almost perfect butt joint, thereby providing more favorable conditions for tissue regeneration and for a faster rate of tissue heating with a more elastic scar.

As different from the prior art instrument, the proposed instrument also permits butt-suturing of solid organs.

The proposed instrument is far simpler in handling than the prior art one: it takes almost half as many manipulations and much less time for stitching organs as the prior art instrument.

The design of the means for grasping and fixing the walls of the organs being stitched in the proposed instrument ensures secure grasping of tissues in the course of stitching, eliminates the possibility of injuring tissues after stitching, and makes it impossible to disengage the instrument from the stitched organs. The locking device employed in the proposed instrument prevents the instrument clamps from being joined for organ stitching until the organ walls are fixed. The device for mutually aligning the organs being stitched in a longitudinal direction relative to the clamp jaws which is provided with movable and stationary stops improves the accuracy of alignment of the organs being stitched and reduces the probability of leaving some portions of the organs unstitched; furthermore, this device simplifies the process of positioning the organs to be stitched between the jaws of the clamps.

The particular design of the lock means maintaining the clearance between the clamp jaws which are composed of irregularly shaped lath springs secured to one of the clamp jaws and stepped recesses provided in the other jaw, provides for atraumatic clinching of the organs to be stitched in a wide range of organ wall thicknesses, and also enables the surgeon to adjust the arrangement of the layers of the sutured organ walls.

Simplified handling procedures, elimination of the danger of grasping the walls of the stitched organs while withdrawing the instrument from the surgery wound, use of the locking device, higher accuracy of alignment of the organ portions being stitched, and some design features which make it impossible to make mistakes in assembling the replaceable components, all these factors render the proposed instrument more reliable and convenient in use than the prior art instrument.

The proposed instrument is provided with replaceable and interchangeable magazines, which allows several anastomoses to be applied in the course of surgery without recharging the magazines with staples. The stitching arrangement of the instrument is failsafe and guarantees reliable stitching of organs and tissues with the staples guaranteed to be fully ejected from the magazine.

The design of the proposed instrument permits reducing the cross-sectional size of the clamp jaws, which improves its maneuverability and allows the instrument to be used even in case of a limited room beneath the organs being stitched.

The proposed instrument is simpler as far as assembling and disassembling are concerned; it is also more amenable to cleaning. Use of the means for grasping the organ walls incorporating toothed plates rigidly coupled with the cases of the means and needles which cooperate with longitudinal through holes in the plate teeth largely reduces the number of replaceable components and makes the instrument more convenient in maintenance.

The proposed instrument is easier to manufacture. The clamp jaws, the magazine components and the dies, all have plane surfaces and are more amenable to machining.

The design of the proposed instrument allows reducing its weight by almost two times as compared to the prior art one, the construction materials being the same.

BRIEF DESCRIPTION OF THE DRAWINGS

The invention will be further understood and its various advantages more fully appreciated from the following detailed description of several exemplary embodiments thereof taken in conjunction with the accompanying drawings, wherein:

FIG. 9 is a magazine, in accordance with the invention;

FIG. 10 shows a portion of the clamp jaw with a recess for the magazine, in accordance with the invention;

FIG. 11 is a sectional view taken along the line XI—XI in FIG. 3;

FIG. 13 is a sectional view taken along the line XIII—XIII in FIG. 1;

FIG. 14 is a plate with straight fixing needles in the first embodiment of the means for grasping and fixing the walls of the organs being stitched, in accordance with the invention;

FIG. 15 illustrates a case with a plate having curved fixing needles in the first embodiment of the means for grasping and fixing the walls of the organs being stitched, in accordance with the invention;

FIG. 16 is a view taken along the arrow XVI in FIG. 15;

FIG. 17 is a schematic representation of the arrangement of the plates with straight and curved fixing needles set to the initial position;

FIG. 18 is a schematic representation of the arrangement of the plates with straight and curved fixing needles set to the working position;

FIG. 23 illustrates a case with a toothed plate;

FIG. 24 shows a needle;

FIG. 25 is a schematic representation of the interaction of the toothed plates of the means for grasping and fixing the walls of the organs being stitched according to the second embodiment, shown at the instant of clinching the organ walls between the clamp jaws;

FIG. 26 is a schematic illustration of the organ walls clinched between the toothed plates and fixed with the aid of "the plate needles";

FIG. 27 shows a needle with a handle (the dot-and-dash line illustrates the curved portion of the needle tip set to be removed from the handle);

FIG. 28 is a side elevation view of a needle with a handle;

FIG. 29 is a sectional view taken along the line XXIX—XXIX in FIG. 19;

FIG. 30 is a sectional view taken along the line XXX—XXX in FIG. 19;

FIG. 31 is a view of the guides and the case of the means for grasping and fixing the walls of the organs being stitched according to the second embodiment with the case fixed in its forward position in accordance with the invention;

FIG. 38 a and b schematically represent the operation of the instrument in accordance with the invention at the instant of clinching organs while performing stitching in the side-to-side method; and FIG. 39 illustrates organs stitched by means of the instrument in accordance with the invention in the side-to-side method.

DETAILED DESCRIPTION OF THE PREFERRED EMBODIMENT

Figure 1:
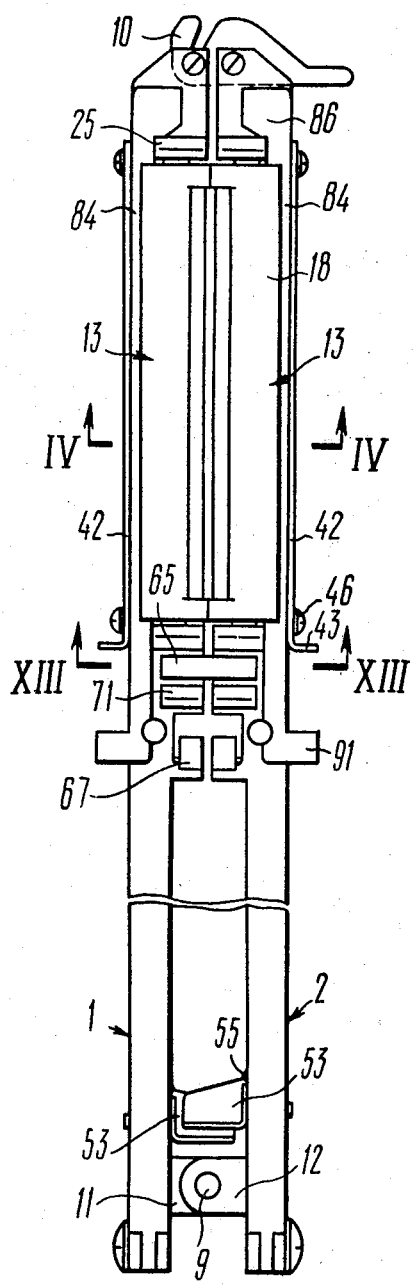
FIG. 1 illustrates a surgical instrument for stitching organs with metal staples, in accordance with the invention.

Referring now to the drawings, the proposed surgical instrument form stitching organs with the aid of metal staples comprises two clamps 1 and 2 (FIG. 1) pivotally interconnected at one end. The clamp 1 comprises jaws 3 and 4 (FIG. 2) and the clamp 2 (FIG. 3) comprises jaws 5 and 6, said jaws being disposed, with the clamps closed, in pairs with one jaw opposite another, the jaw 3 (FIG. 4) of the clamp 1 opposite the jaw 5 of the clamp 2, while the jaw 4 opposite the jaw 6.

The joint line I—I of the jaws 3 and 4, 5 and 6 of the clamps 1 and 2 is perpendicular to the joint line II—II of the clamps 1 and 2.

Between the butt surfaces 7 of the jaws 3, 4, 5 and 6 of each clamp 1 and 2 there is provided a clearance corresponding to the thickness of the tissues to be clinched. The clamps 1 and 2 are also so interconnected that there is provided a clearance between butt surface 8 thereof. The clamps 1 and 2 are interconnected with the aid of a split hinge latch 9 (FIG. 1) at one end and locking hooks 10 at the opposite end. The pin and hole of the split hinge latch 9 are disposed on lugs 11 and 12 rigidly coupled with the clamps 1 and 2, respectively, the axis of the split hinge latch 9 being perpendicular to the joint line I—I (FIG. 4) of the jaws 3 and 4, 5 and 6 of the clamps 1 and 2. Such a design clearly shows the connectible components of the split hinge latch 9 (FIG. 1), providing convenient means of closing the clamps 1 and 2 in the course of surgery.

The surgical instrument of this invention comprises a means 13 for grasping the walls of the organs being stitched, magazines 14 (FIG. 4) with slots for staples, pushers 15 and dies 16 with recesses for bending the staples, all of the above members being mounted on the jaws 3, 4, 5 and 6 of the clamps 1 and 2. The magazines 14 and the dies 16 cooperating at the instant of stitching are disposed on the paired jaws 3 and 5, 4 and 6 of different clamps 1 and 2. The instrument also comprises a device 17 (FIG. 3) for mutually aligning the organs being stitched in a longitudinal direction with respect to the jaws.

Figure 7:
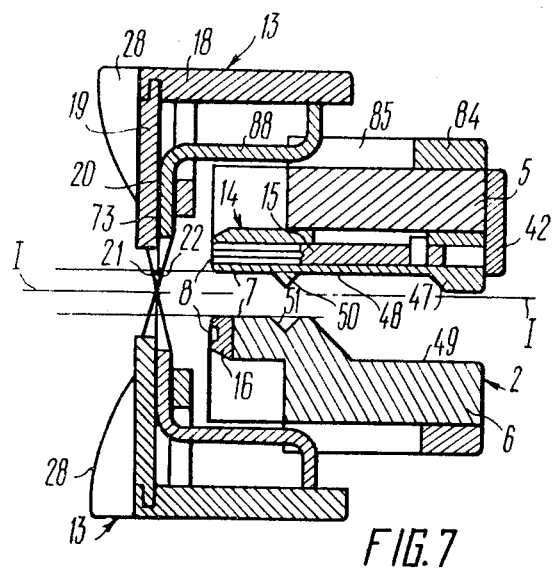
FIG. 7 is a sectional view taken along the line VII—VII in FIG. 5.

The means 13 (FIG. 1) for grasping the walls of the organs being stitched is formed as cases 18 (FIGS. 3, 4 and 5) which, in one of the embodiments of the instrument in accordance with the invention, incorporate each two built-in toothed plates 19 and 20 (FIG. 4) with teeth 21 and 22 for grasping and fixing the walls of the organs being stitched. In a general case, the design, the type of interconnection of the plates and the type of connection thereof with the case 18, as well as the number of plates in each case 18 of the means 13 and the design of the plate teeth, may all vary. However, a characteristic and common feature of the instrument in accordance with the invention consists in that the cases 18 are mounted on each jaw 3, 4, 5 and 6 in guides 23 (FIG. 6) providing for a limited degree of movability of each of said cases 18 in a plane perpendicular to the joint line I—I (FIG. 4) of the jaws 3, 4, 5 and 6 of the clamps 1 and 2 and to the joint line II—II of the clamps 1 and 2 so that each of the cases 18 may be set to either to two extreme positions. In one of such extreme positions, a forward one illustrated in FIG. 7 and corresponding to the instant of clinching and grasping the walls of the organs being stitched with the clamps 1 and 2 set apart, the tips of the teeth 21 and 22 of the toothed plates 19 and 20 are disposed between the butt surfaces 7 of the jaws 5 and 6 (or 3 or 4, not shown in FIG. 7) and somewhat in front of the butt surfaces 8 of the clamps 1 and 2. In the other extreme position of the cases 18 a backward one illustrated in FIG. 4 and corresponding to the instant of placing sutures with the clamps 1 and 2 joined, the tips of the teeth 21 and 22 are disposed a certain distance from the butt surfaces 7 of the jaws 3 and 4, 5 and 6 of the clamps 1 and 2, respectively, and approximately in the planes of the butt surfaces 8 of the clamps 1 and 2.

With the proposed instrument so designed, after the walls of the organs being stitched have been clinched separately with each clamp 1 and 2, the organ wall portions freely lying in front of the butt surfaces 8 of the clamps 1 and 2 at a predetermined distance therefrom can be grasped with the aid of the means 13; and after the organ portion to be excised has been cut off and the clamps 1 and 2 joined, the edges of the clinched organs being stitched can be set apart and placed between the cooperating magazines 14 and dies 16, uniformly aligning the walls of the organs being stitched. A possibility is likewise provided of positioning the fixing teeth 21 and 22 of the means 13, and hence the edges of the organs being stitched, at a minimum distance from the suture line, thereby enabling the walls of hollow organs to be stitched with the anastomosis suture line lying at a minimum distance from the edge of the walls of the sutured organs, i.e. guaranteeing almost butt-stitching. Also, this feature allows butt-stitching solid organs and tissues with the two linear staple sutures being disposed on the side of the organ walls.

The guides 23 (FIG. 6) are formed as closed through slots with inclined portions 24 formed in supports 25 and pins 26 fitted into the slots and secured to the side faces of the case 18. The supports 25 positioned on both sides of the case 18 are fixed on the clamp jaws, e.g. on the jaw 5, as shown in the drawing. The closed slots of the guides 23 also have small portions 27 parallel to the butt surfaces 7 of the clamp jaws. These are designed for improving the dependability of fixation of the cases 18 in the extreme positions. With the guides 23 formed as closed slots with the inclined portions 24 and the pins 26 on the cases 18 cooperating therewith, the cases 18 can be moved without fail from one extreme position to the other.

While moving from one extreme position to the other, the case 18 simultaneously turns in a transverse plane perpendicular to the butt surfaces 7 of the jaws 3, 4, 5 and 6 of the clamps 1 and 2 (FIG. 4) and to the butt surfaces 8 of the clamps 1 and 2, thereby permitting reducing the cross section of the working part of the jaws 3, 4, 5 and 6 of the closed clamps 1 and 2, hence permitting reducing the minimum required room beneath the sutured organs wherein the working part of the instrument jaws can be disposed.

Figure 4:
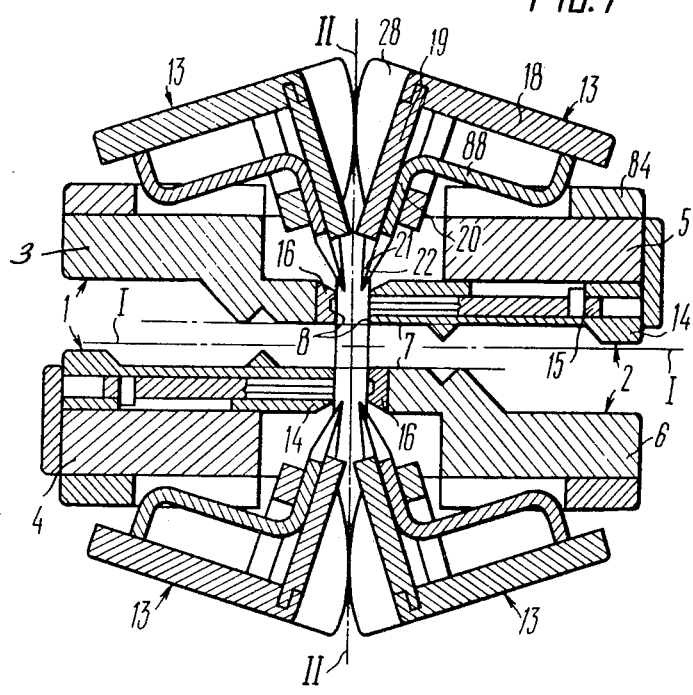
FIG. 4 is a sectional view taken along the line IV—IV in FIG. 1.
Figure 8A:
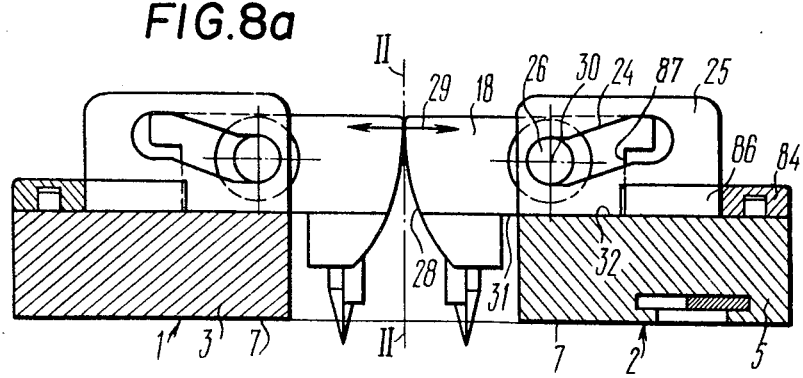
FIG. 8 a, b and c illustrate the successive arrangements of the cases of the means for grasping and fixing the walls of the organs being stitched while the clamps are being closed, in accordance with the invention.
Figure 8B:
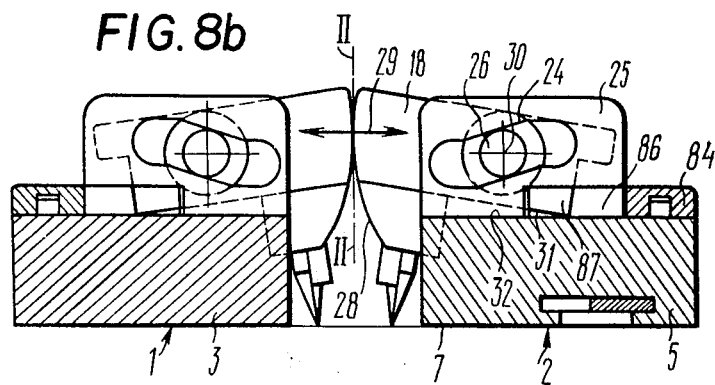
Figure 8C:
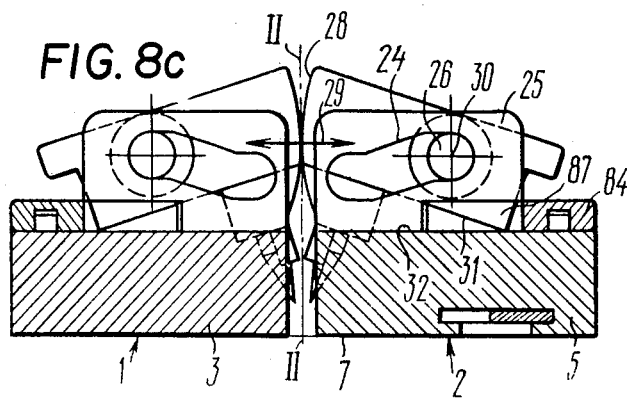

Each of the cases 18 is provided with cam projections 28 disposed on the side of the joint line II—II of the clamps 1 and 2, which cam projections 28 cooperate with respective similar cam projections 28 on the cases 18 of the opposite clamp 1 or 2. Therefore, as the clamps 1 and 2 are closed for stitching, the cases 18 are simultaneously moved from their forward positions (FIG. 7) to their backward positions (FIG. 4). The shape and layout of the cam projections 28 are so selected that at any instant of interaction of the cam projections 28 (FIG. 8a, b and c) of the opposite cases 18 caused by the closing of the clamps 1 and 2, forces 29 exerted thereon are directed eccentrically with respect to axes 30 of the pins 26. The forces 29 exerted on the cases 18 are shifted, with respect to the axes 30, in such a direction as to ensure the turning and transfer of the cases 18 from their forward positions in which the walls of the organs being stitched are fixed to their backward positions in which stitching is performed. In a particular case, the profile of the cam projections 28 illustrated in the accompanying drawings is an arc of a circumferenced.

The case 18 is provided with a bearing surface 31 cooperating with surface 32 of the jaw whereon it is secured and providing a support making for the movement of the cases 18 from one extreme position to the other.

The magazines 14 (FIG. 4) and dies 16 are fixed on the jaws of the clamps 1 and 2.

The magazines 14 (FIGS. 4 and 9) are formed as flat cartridges disposed in a depression 33 (FIG. 10) formed in the jaws 4 and 5 (FIG. 4) on the side of their butt surfaces 7. Each magazine 14 has a longitudinal through slot 34 (FIGS. 9 and 11) perpendicular to slots 35 for the staples (not shown) whereinto the staple pushers 15 (FIG. 11) are fitted. The staple pushers 15 are provided with a drive 36 formed as a plate so secured to the jaw 4 or 5 (FIG. 4) as to be able to move within the longitudinal through slot 34 (FIG. 11) of the magazine 14. On the front end of the drive 36 of the pushers 15 there is provided a wedge-shaped chamfer 37 which, as the drive 36 moves in the longitudinal slot 34 of the magazine 14, acts on the pushers 15, urging them to force the staples out of the magazine 14. With the magazine 14, the pushers 15 and the drive 36 so designed, the staples are guaranteed to be fully forced out of the magazine 14.

The instrument magazines 14 are replaceable and interchangeable, so that multiple sutures may be placed in the course of surgery without recharging the magazines 14 with staples. Each magazine 14 is provided with transverse external projections 38 (FIG. 9) with stops 39, and the jaws 4 and 5 (FIG. 10) have transverse recesses 40 whereinto are fitted the projections 38 (FIG. 9) of the magazine 14 until the projection stops 39 come into contact with wall 41 (FIG. 10) of the jaw 4 or 5. The magazine 14 (FIG. 11) fitted into the jaw 4 or 5 is secured thereto with the aid of a locking plate 42 having a handle 43 and a closed longitudinal opening 44 (FIG. 2) at one end and a fork 45 at the other end. The locking plate 42 is secured to the jaw 4 by means of two T-shaped pins 46 cooperating with the opening 44 and the fork 45 in such a way as to enable the locking plate 42 to move lengthwise to disengage the fork 45 from the pin 46 and then to turn to release the magazine 14 if it is to be removed from the jaw 4. The magazine 14 is provided with a longitudinal projection 47 (FIG. 9) facilitating the task of removal of the magazine 14 from the jaw 4.

Surface 48 of the magazine 14 serves as a tissue-clinching surface of the jaw whereto the magazine 14 is secured. In order to limit the area of organ clinching between the clamp jaws, the tissue-clinching surface of the jaw 3 or 6 (FIG. 7) whereto the die 16 is secured is formed to have a longitudinal recess 49 on the reverse side relative to the butt surface 8. A widened portion is formed on this side between the jaws 5 and 6, just as it is formed between the jaws 3 and 4 (FIG. 4), thanks to which the organs to be stitched are clinched between the butt surfaces 7 of the jaws 5 and 6, 3 and 4 in a narrow band, narrower than the jaws 3, 4, 5 and 6. And in order to ensure that the organ walls adhere more firmly to the butt surfaces 7, thereby preventing the clinched organs from slipping free, the magazine 14 is provided with a longitudinal projection 50 (FIG. 7) cooperating with a longitudinal groove 51 on the butt surface 7 of the jaw 6 carrying the die 16.

The drives 36 (FIG. 11) of the pushers 15 are dismountably secured to the jaws with the aid of detachable plates 52.

The drive 36 of the pushers 15 is equipped with a handle 53 which is represented by the curved back portion of the plate from which the drive 36 is constructed. The handle 53 has a springy section 54 (FIGS. 3 and 5) cooperating with a projection 55 on the jaw 5, which projection 55 serves for fixing the drive 36 in the initial position thereof. In the initial position, the handle 53 is disposed, relative to the fixing projection 55, on the side opposite to the position of the magazine 14 (FIG. 11), whereas the wedge-shaped front end 37 of the drive 36 rests in slot 56 of the jaw 5, which slot 56 is a continuation of the longitudinal slot 34 of the magazine 14. In this position, the wedge-shaped front end 37 of the drive 36 is outside of the longitudinal slot 34 of the magazine 14, and the latter can thus be removed from the jaw 5. The fixing projection 55 blocks the handle 53 of the drive 36 from moving towards the magazine 14, preventing accidental movement of the drive 36 and accidental forcing of the staples out of the magazine 14. It is only after the springy section 54 of the handle 53 passes through the fixing projection 55 that, by exerting a definite effort on the handle 53, is it possible to introduce the wedge-shaped front end 37 of the drive 36 into the longitudinal slot 34 of the magazine 14 and apply it to the pushers 15 in order to force the staples out of the transverse slots 35 of the magazine 15.

Figure 12:
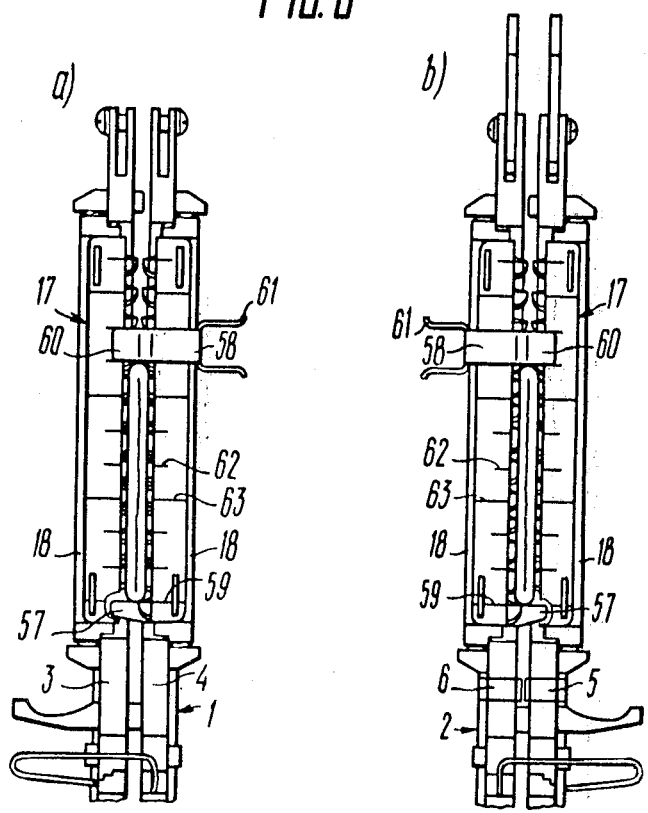
FIG. 12 a and b illustrate set-apart clamps with a device for aligning the organs being stitched lengthwise relative to the jaws, in accordance with the invention.

The device 17 (FIGS. 3 and 12) for mutually aligning the organs to be stitched in a longitudinal direction relative to the jaws comprises two components, one disposed on the clamp 1 (FIG. 12a) and the other on the clamp 2 (FIG. 12b) and incorporates stationary stops 57 (FIG. 12 a and b) and movable stops 58 between which are positioned the organ portions to be aligned as the latter are clinched by the jaws 3, 4, 5 and 6 of the clamps 1 and 2, as well as scales 59 whose graduation notches are arranged longitudinally with respect to the jaws 3, 4, 5 and 6 of the clamps 1 and 2 and accurately matched on the cooperating jaws 3 and 5, 4 and 6. In the particular embodiment of the proposed instrument illustrated in the accompanying drawings, the stationary stops are fixed on the case 18 of the jaw 4 of the clamp 1 and on the case 18 of the jaw 6 of the clamp 2 and are disposed immediately close to the starting graduation notches of the scales 59.

The movable stops 58 are replaceable and may be mounted on the case 18 so as to be movable and fixable relative to the scales 59. The replaceable movable stops 58 are formed as a curved plate with a projection 60 springing in a transverse direction relative to the jaw and handles 61 serving to assist in positioning the stops 58 relative to the scales 59 and to provide a hold on the stops 58 being removed from the cases 18.

The stationary stops 57 delimit and help accurately align the edges of the semiperimeters of the organs clinched between the jaws 3 and 4, 5 and 6 of each clamp 1 and 2 on one side, and the movable stops 58 on the other side.

Figure 2:
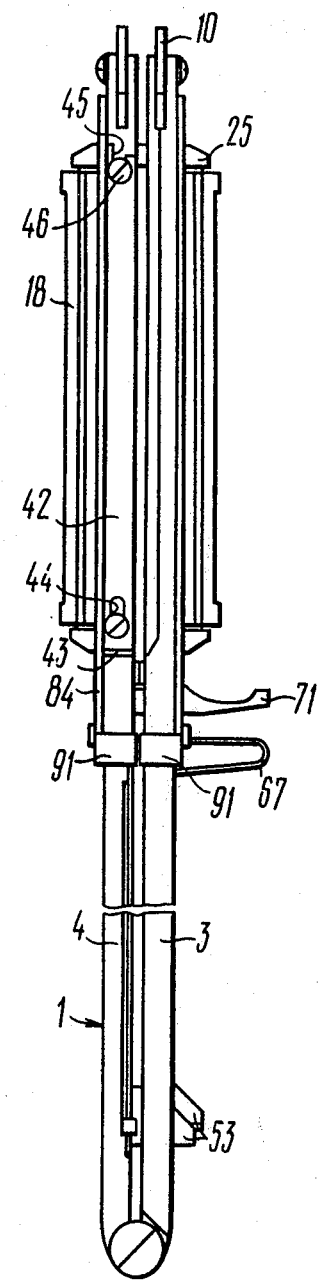
FIG. 2 is a side elevation view of a surgical instrument for stitching organs with the aid of metal staples, in accordance with the invention.

The movable stops 58 are positioned by the graduation notches of the scales 59 in accordance with the size of the organ portions to be stitched; depending on the type of surgical procedure, the movable stops 58 may be employed either on one of the clamps, 1 or 2, or on both clamps 1 and 2 at the same time. At the instant of stitching, with the clamps 1 and 2 closed, as shown in FIGS. 1 and 2, the movable stops 58 (FIG. 12) are removed from the clamps 1 and 2.

For the convenience of the surgeon some of the graduation notches of the scale 59 are made short, such as graduation notches 62, whereas others are long, such as graduation notches 63. The distance between each two graduation notches 62 of the scale 59 is equal to the spacing of the staples in the suture being placed. The long graduation notches 63 are arranged at intervals equal to three times the staple spacing; it is preferred that each long graduation notch 63 should be marked by a numerical designation showing its distance from the zero notch on the scale 59. The a scale 59 enables the surgeon to position without errors the movable stops 58 on the clamps 1 and 2 to conform to the predetermined size of the sutures being placed; it also permits sufficiently accurately determining the position of the second edge of the organ clinched by the first clamp 1 or 2 with respect to the first edge positioned by the stationary stop 57 and by the zero notch on the scale 59, as well as positioning the movable stop 58 of the second clamp 2 or 1, respectively, at the same distance. The graduated scales 59 of the means 17 for mutually aligning the organs being stitched in a longitudinal direction relative to the jaws 3, 4, 5 and 6 of the clamps 1 and 2 enable the surgeon to determine with a high degree of precision the size of the placed sutures, e.g. the size of the anastomosis in stitching hollow organs, and also, the distance between each two graduation notches on the scales corresponding to the staple spacing, to determine precisely the number of staples in the suture, which is often required for postoperative X-ray studies of the state and alteration of the sutures applied.

In the particular embodiment of the proposed instrument shown in the drawings, the jaws 3 and 4, 5 and 6 of each clamp 1 and 2 are interconnected by means of a hinge joint 64 (FIG. 3) mounted on the ends of the clamps 1 and 2.

However, the clamp jaws according to the invention may likewise be interconnected in a different way, e.g. with the aid of guides providing for the translation of the jaws one towards the other as they are closed or set apart (not shown).

In order to fix the paired jaws 3 and 5, 4 and 6 of the clamps 1 and 2 relative to each other and to ensure accurate alignment of the magazines 14 (FIG. 4) and the dies 16 in the course of stitching, with the clamps 1 and 2 being joined, the instrument is provided with two forks 65 and 66 (FIG. 13) rigidly secured to the middle portion of the jaws 5 and 6 of the clamp 2 and enveloping with their prongs the jaws 3 and 4 of the clamp 1, said prongs being formed as plane-parallel plates. With the paired jaws 3 and 5, 4 and 6 of the clamps 1 and 2 being mutually fixed with the aid of the forks 65 and 66, the surgeon has a good view of the connectible members, which consequently simplifies the operation of clamp closing in the course of surgical intervention and also simplifies the task of cleaning the instrument.

In the exemplary embodiment of the instrument presented herein, each of the clamps 1 and 2 is provided with a lock means for fixing the clearance between the jaws 3, 4, 5 and 6 formed in clinching the organ to be stitched. This clearance-fixing means comprises an irregularly shaped lath spring 67 (FIG. 3) having one end 68 thereof rigidly secured to one of the clamp jaws, e.g. jaw 6, and stepped recesses 69 formed in the other jaw, e.g. jaw 5, and cooperating with the other free end 70 of the spring 67.

Depending on the particular recess 69 against which the free end 70 of the spring 67 rests, the clearance between the jaws, e.g. jaws 5 and 6, varies, which causes the clearance between the fixing teeth 21 and 22 of the opposite jaws to vary as well. As organs with a variable wall thickness are clinched between the jaws 5 and 6, the clearance between said jaws is continuously varied through the deformation of the spring 67. Such a design of the lock means for fixing the clearance between the jaws 5 and 6 provides for atraumatic clinching of the walls of the organs being stitched in a wide range of organ wall thicknesses; it also makes for the convenience of use of the clamps in the course of surgery, as the springs 67 automatically close the jaws 5 and 6 while the organ to be stitched is being clinched.

With one of the clamp jaws having the stepped recesses 69 and the other jaw having the irregularly shaped spring 67 whose free end 70 cooperates with one of the stepped recesses 69 of the former jaw, it is likewise possible to vary the depth to which the teeth 21 and 22 of the means 13 for grasping and fixing the walls of the organs being stitched penetrate into the wall of the organ clinched between the clamp jaws, which in turn allows of changing the arrangement of the layers of the aligned organ walls set to the position for stitching. Hence, the surgeon is able to preset the optimal arrangement of the layers of the walls of the stitched organs depending on the specific characteristics (thickness, properties, etc.) of the walls of the organs being stitched.

To facilitate the setting apart of the jaws 6 and 5 of the clamp 2, and also the jaws 3 and 4 of the clamp 1 (not shown), the free end 70 of the spring 67 protrudes beyond the jaw 5 with its stepped recesses 69 after the stitching operation is over and the walls of the stitched organs have been released. The jaw 5 is provided with a handle 71 having a recess 72. The handle 71 is disposed next to the protruding free end 70 of the spring 67 so that, as the handle 71 and the spring 67 are pressed together, the free end 70 of the spring 67 is disengaged from the stepped recess 69. This automatically causes the jaws 6 and 5 of the clamp 2 to be set apart, for the protruding end 70 of the spring 67 being pressed against the handle 71 assumes an inclined position, generating forces which drive the jaws 5 and 6 apart.

The handle 71 is secured to the clamp jaw which occupies a position above the organs being stitched, so that the handle 71 simultaneously provides support for the surgeon's fingers pressing on the handles 53 of the drives 36 (FIG. 11) of the pushers 15.

The drawings illustrating the surgical instrument for stitching organs in accordance with the invention present two embodiments of the means for grasping and fixing the walls of the organs being stitched, although the possible number of feasible embodiments designed to meet concrete application conditions can be much greater.

In the first embodiment, the means 13 (FIG. 7) for grasping and fixing the walls of the organs being stitched incorporates the two cooperating toothed plates 19 and 20 built into each of the cases 18 and adjoining each other by way of lateral surfaces 73 thereof.

The teeth 21 and 22 of the plates 19 and 20 are formed as fixing needles. The teeth 21 are arranged at equal intervals on surface 74 (FIG. 14) of the longitudinal edges of the plates 19; they are made straight and approximately perpendicular to the surface 74. The teeth 22 (FIG. 15) are arranged on surface 75 of the longitudinal edges of the plates 20 at the same intervals as the teeth 21 (FIG. 14). The teeth 22 (FIG. 15) are curved in one direction opposite to the position of the hinge 64 (FIG. 3), i.e. in a direction opposite to the supposed direction of withdrawal of the instrument from the surgery wound.

Thanks to the latter design feature, the tissues cannot be grasped by the fixing needles while the instrument is being withdrawn from the surgery wound, thereby avoiding injuring the organ walls after stitching.

The plate 19 (FIG. 14) with the straight teeth 21 is provided with projections 76 which, when coupled with the case 18 (FIG. 15), are disposed in grooves 77 formed in the case 18. The plate 20 with the curved teeth 22 is disposed in a recess 78 formed in the case 18. The plate 19 (FIG. 16) is fixed to the case 18, while the plate 20 is slidably coupled with the case 18; the plate 20 able to move in a longitudinal direction is mounted beneath the plate 19. Longitudinal openings 79 are formed in the plate 20 (FIG. 15) with the curved teeth 22, which longitudinal openings 79 receive guide pins 80 and 81 rigidly connected with the case 18. This feature enables the plate 20 with the curved teeth 22 to slide along the case 18 and the plate 19 (not shown in FIG. 15) with the straight teeth 21 until contact with wall 82 of the case 18, so that the plate 20 can be set to either one of two positions: an initial position and a working position.

With the plate 20 set to the initial position (FIG. 17), the teeth 21 and 22 adjoin one another by way of the tips thereof, defining closed contours, which obviates any possibility of injuring the surgeon's hands as well as the tissues, both those tissues which are being fixed and the surrounding tissues, with the sharp teeth 21 and 22 protruding the plane of the clamp jaws while the instrument is being manipulated. With the plate 20 set to the working position shown in FIG. 18, the plate 20 is displaced relative to the initial position by the spacing between the teeth 21 and 22, so that the curved teeth 22 are displaced relative to the straight teeth 21 with which they are in contact in the initial position also by the spacing between the teeth and come to adjoin with their tips the adjacent straight teeth 21 of the plate 19.

The plates 19 with the straight teeth 21 and the plates 20 with the curved teeth 22 are dismountably coupled with the case 18 (FIG. 15). In order to prevent faulty assembly of the plates 19 and 20 of different clamp jaws, the longitudinal openings 79 of the plate 20 with the curved teeth 22 are arranged asymmetrically along the length of the plate 20, the height of the guide pin 80 does not exceed the thickness of the plate 20, the pin 81 is higher than the plate 20, and the plate 19 comprises a transverse recess 83 corresponding to the pin 81.

Figure 5:
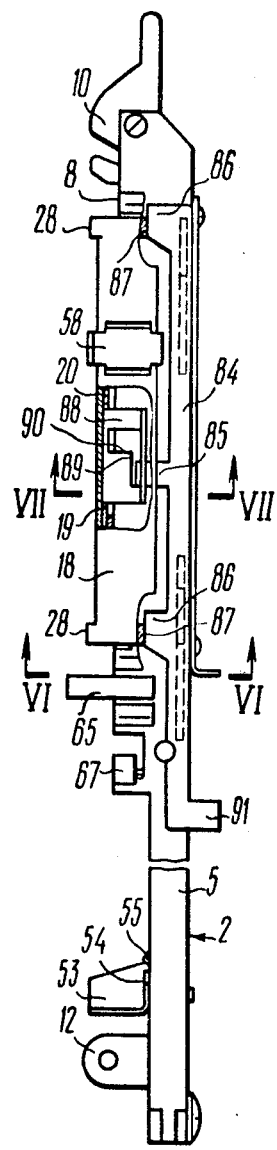
FIG. 5 is a view taken along the arrow V in FIG. 3.
Figure 6:
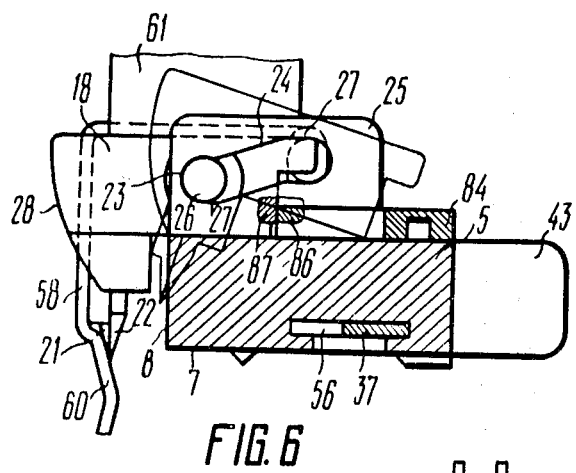
FIG. 6 is a sectional view taken along the line VI—VI in FIG. 5.

Each of the clamp jaws comprises a locking device designed to prevent the instrument clamps from being manipulated to close the clamps to perform stitching of the organ walls in case the latter are unfixed, and also serving as the drive of the movable plate 20 (FIG. 15) with the curved teeth 22. Said locking device is formed as a plate 84 with a dog 85 cooperating with the movable plate 20 and also having stops 86 cooperating with projections 87 on the case 18 whose cam projections 28 in the forward position are disposed at a distance from the butt surface 8 of the clamp 2 exceeding half the stitching clearance, the latter being equal to the clearance between the butt surfaces 8 of the closed clamps. Said plate 84 is mounted along the jaw, e.g. jaw 5 (FIG. 5). The slidable plate 20 has a curved portion 88 with an L-shaped slot 89 cooperating with the dog 85.

The plate 84 occupies either one of two extreme positions determining two positions of the plate 20 in which the curved teeth 22 (FIG. 17) are either drawn back from the paired straight teeth 21 of the plate 19 or adjoin them for fixing the organ walls. With the plate 84 occupying one extreme position, the dog 85 fixes the plate 20 in the initial position and the stops 86 fix the case 18, preventing its displacement by pressing the case 18 through the projections 87 and pins 26 (FIG. 6) of the case 18 against the walls of the slots 23 of the supports 25. With the plates 84 so positioned (FIG. 5), the clamps cannot be closed for setting the organ walls to the position for stitching, for they are prevented therefrom by the cam projections 28 of the cases 18 pressing on one another, the cases 18 being immobilized on the jaws by means of the stops 86 of the plates 84.

With the plate 84 set to its second extreme position (FIGS. 1 and 2), the dog 85 (FIG. 5) presses (not shown in the drawing) the plate 20 against the lateral wall 82 (FIG. 15) of the recess 78 of the case 18, securing it against displacement, the paired curved teeth 22 and the straight teeth 21 (FIG. 18) of the plates 20 and 19 being closed, i.e. set to the position for grasping tissues. The dog 85 (FIG. 5) of the plate 84 registers with a transverse notch 90 of the L-shaped slot 89 of the plate 20, and the stops 86 are brought out of engagement with the projections 87 of the case 18, releasing the latter. When the case 18 is set to the position for stitching (FIG. 4), the cam projections 28 of the case 18 are spaced from the butt surfaces 8 of the clamps 1 and 2 (the surfaces of the magazine 14 and the die 16) which are aligned for stitching by a distance equal to or smaller than half the stitching clearance, owing to which the clamps 1 and 2 can be joined for stitching after the organ walls have been fixed.

The plate 84 (FIGS. 1 and 2) is moved from one extreme position to the other with the aid of handles 91 which are represented by the curved portion of the plate 84. The handles 91 of both jaws of each clamp 1 and 2 are disposed next to each other and protrude the plane of the jaws, making for the convenience of manipulation of the plates 84 and permitting both semiperimeters of the walls of the clinched organ to be simultaneously fixed in one movement.

Figure 19:
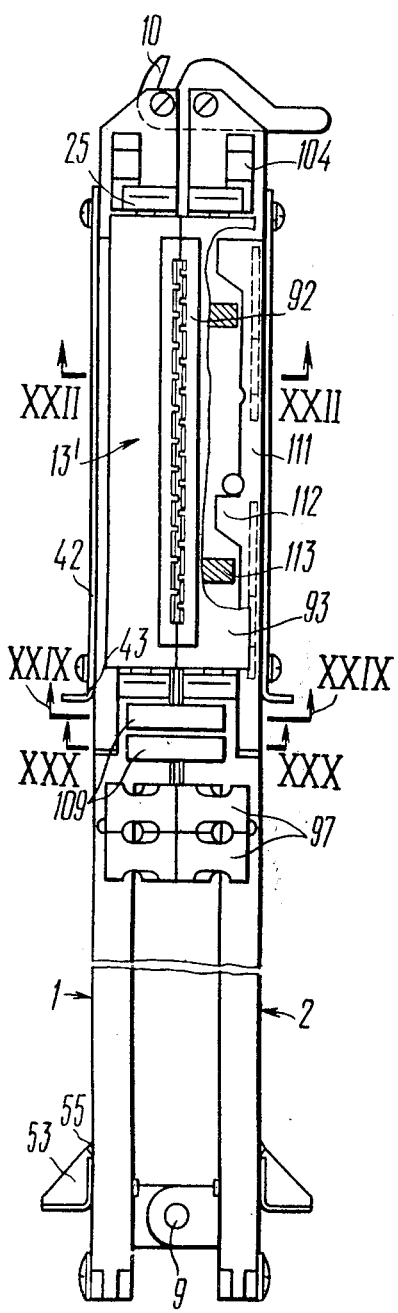
FIG. 19 is a surgical instrument for stitching organs with the aid of metal staples, in accordance with the invention, incorporating a means for grasping and fixing the walls of the organs being stitched according to the second embodiment.
Figure 20:
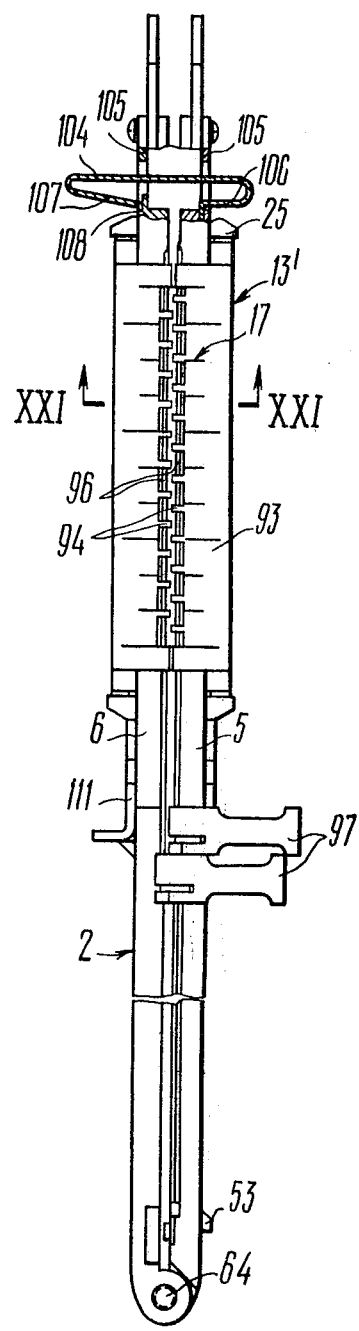
FIG. 20 is a clamp of the proposed surgical instrument comprising a means for grasping and fixing the walls of the organs being stitched according to the second embodiment, in accordance with the invention.
Figure 21:
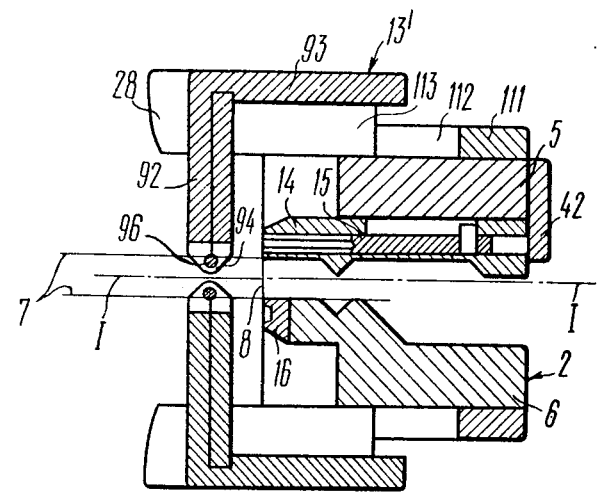
FIG. 21 is a sectional view taken along the line XXI—XXI in FIG. 20 (shown turned at 90°)
Figure 22:
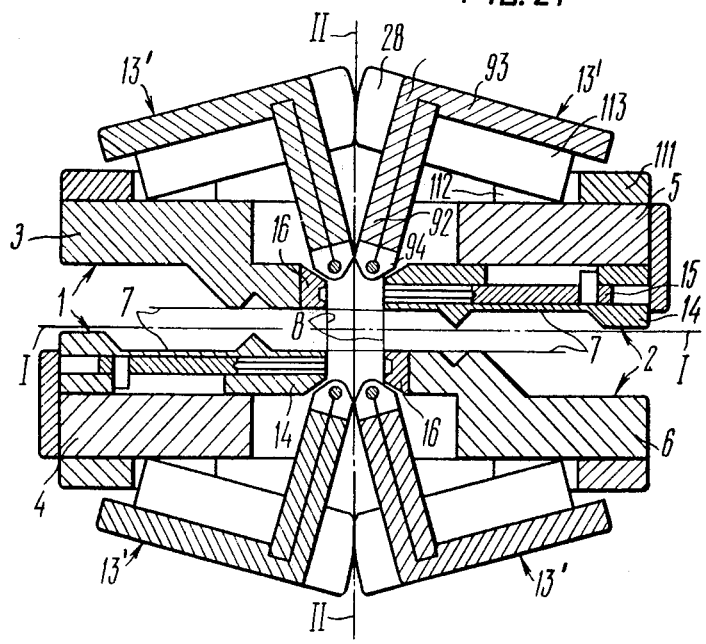
FIG. 22 is a sectional view taken along the line XXII—XXII in FIG. 19.

In the second embodiment, the means 13' (FIGS. 19 and 20) for grasping and fixing the walls of the organs being stitched incorporates toothed plates 92 (FIGS. 21 and 22) fixed on cases 93 of the means 13', i.e. they are built integral with the cases 93, which considerably reduces the number of detachable instrument components which must be removed for cleaning purposes and also simplifies maintenance. Teeth 94 of the plates 92 have coaxial through holes 95 (FIG. 23) into which a needle 96 (FIGS. 20 and 24) is fitted. The teeth 94 (FIGS. 20 and 25) of the plate 92 of the case 93 of one clamp jaw in the embodiment in question are displaced with respect to the teeth 94 of the appropriate plate 92 of the second clamp jaw so that the organ walls clinched between the toothed plates 92 are crimped by the teeth 94 of the opposite plates 92. When the needles 96 (FIG. 26) are fitted into the holes 95 of the teeth 94 on both clamp jaws, one needle 96 transfixes one wall of the clinched organ, while the other needle pierces the opposite wall.

In the embodiment in question, the needles 96 (FIGS. 26 and 20) are detachably coupled with the instrument and provided with handles 97 (FIGS. 27 and 28) making for the convenience of fitting the needles into the openings 95 (FIG. 23) of the plates 92 and of withdrawing them therefrom. In order that the worn-out needles may be easily replaced, the needle 96 is detachably coupled with the handle 97. End 98 (FIG. 24) of the needle 96 is curved and represents an irregularly shaped spring with a curved portion 99 serving as a stop after the needle has been coupled with the handle 97 (FIG. 28) and with a lock means 100 (FIG. 24) arranged in parallelism with the needle 96 and serving to fasten the needle 96 to the handle 97 (FIG. 28). The handle 97 has a hole 101 for receiving the needle 96, a slot 102 wherein the curved stop 99 is disposed, and a groove 103 (FIG. 27) wherein the lock means 100 is mounted. In order to separate the needle 96 and the handle 97, the lock means 100 is withdrawn from the groove 103, the curved portion 99 of the needle 96 is turned approximately through 180° to a position shown in FIG. 27 with a thin line, and the needle 96 is withdrawn from the handle 97.

Each of the clamps 1 and 2 (FIG. 19) of the instrument incorporating the means 13' for grasping and fixing the walls of the organs being stitched according to the second embodiment is provided with a lock means for fixing the clearance between the jaws while clinching the ends of the organ to be stitched, which fixing means is formed as spring catches 104 (FIG. 20) disposed on ends 105 of the jaws 5 and 6, as well as 3 and 4. This design feature obviates the need for the surgeon to press on the ends 105 of the jaws, e.g. the jaws 5 and 6 of the clamp 2, with his fingers to provide for a uniform grasping of the organ walls along the entire working length of the jaws 5 and 6, and also simplifies the task of instrument handling. The catch 104 is formed as an irregularly shaped latch spring having one end 106 secured to the jaw 5 and the other end 107 cooperates with a stepped recess 108 formed in the jaw 6. Actually, the catch 104 is indistinguishable from the irregularly shaped lath spring 67 (FIG. 3) discussed hereinabove while describing the instrument incorporating the means 13 for grasping organ walls according to the first embodiment.

In order to provide for an accurate alignment of the paired jaws 3 and 4 as well as 5 and 6 (FIGS. 29 and 30) of the clamps 1 and 2 after the clamps 1 and 2 have been closed, each jaw comprises a projection 109 cooperating an external surface 110 of the paired jaw of the opposite clamp 1 or 2. Two projections 109 of the jaws of each clamp 1 or 2 define a fork enveloping the surfaces 110 of the jaws of the opposite clamp 2 or 1, respectively.

The cases 93 (FIG. 21) of the means 13' for grasping the walls of the organs being stitched according to the second embodiment can be set, just as the cases of the means 13 according to the first embodiment, to either one of two extreme positions, a forward position in which the organ walls are fixed, and a backward position (FIG. 22) in which stitching is carried out. The means 13' according to the second embodiment is provided with lock means 111 for locking the cases 93 in the forward position, which lock means 111 are formed as plates arranged along the jaws 3, 4, 5 and 6 of the clamps 1 and 2 and able to move lengthwise. Each plate 111 is provided with stops 112 (FIG. 19) cooperating with projections 113 of the case 93 and can be set to either one of two extreme positions. In one extreme position, the stops 112 (FIG. 21) cooperate with the projections 113 of the case 93 to press the pins 26 (FIG. 31) against the wall of the closed slot of the guides 23, thereby fixing the case 93 in its forward position. In the other extreme position, the stops 112 (FIG. 19) are out of contact with the projections 113 so that the case 93 may be moved to its backward position as in FIG. 22 in which the organs are stitched, after the clamps have been brought together and closed.

The instruments in accordance with the invention incorporating the means for grasping the walls of the organs being stitched according to the first and second embodiments, as illustrated in the drawings, are essentially similar, the only differences being in the design of some minor members which have no effect on the operation of the instrument. For this reason the analogous parts and components are denoted in the drawings by the same numerical designations irrespective of the particular embodiment.

The primary considerations behind the design of the components of the proposed instrument are maximum amenability of the instrument to cleaning and washing and minimum difficulties in manufacture.

To this end, the parts and components of the proposed instrument contain no blind holes or slots which usually accumulate dirt. The jaws 3, 4, 5 and 6 of the clamps 1 and 2 are formed as elongated flat bars readily amenable to machining. Most parts are formed as flat plates with curved members, likewise pushers are so designed in accordance with the invention that they can be manufactured both as metal components and as disposable plastic members.

Except for some minor peculiarities, the proposed surgical instrument for stitching organs with the aid of metal staples is manipulated in the same way whether employed for stitching in the end-to-end, end-to-side or side-to-side methods.

While stitching in the end-to-end method, e.g. while applying end-to-end anastomoses to hollow organs, for instance intestines, and if the organs being stitched differ in diameter, one of the clamps, e.g. the clamp 2, is so applied to organ portion 114 (FIG. 32a) having the larger semiperimeter in cross section that one edge of the clinched portion is in contact with the stationary stop 57. The movable stop must be removed from this clamp 2. As the organ is clinched, the spring 67 (FIG. 3) closes the jaws 5 and 6 of the clamp 2, with the free end 70 of the spring 67 resting against one of the stepped recesses 69.

Figure 3:
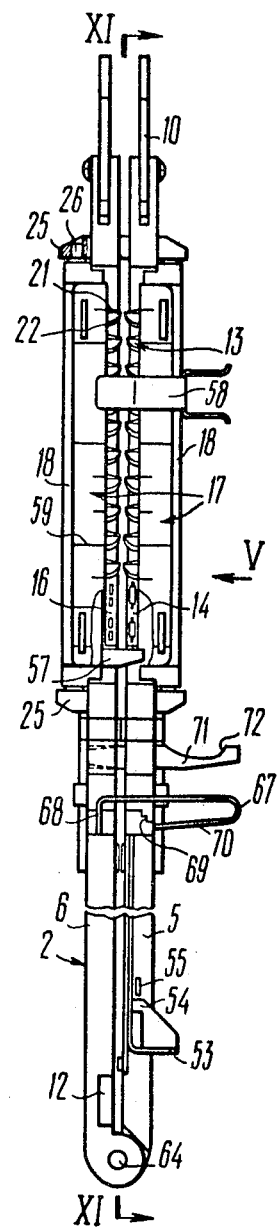
FIG. 3 is a clamp of the surgical instrument, in accordance with the invention.
Figure 32:
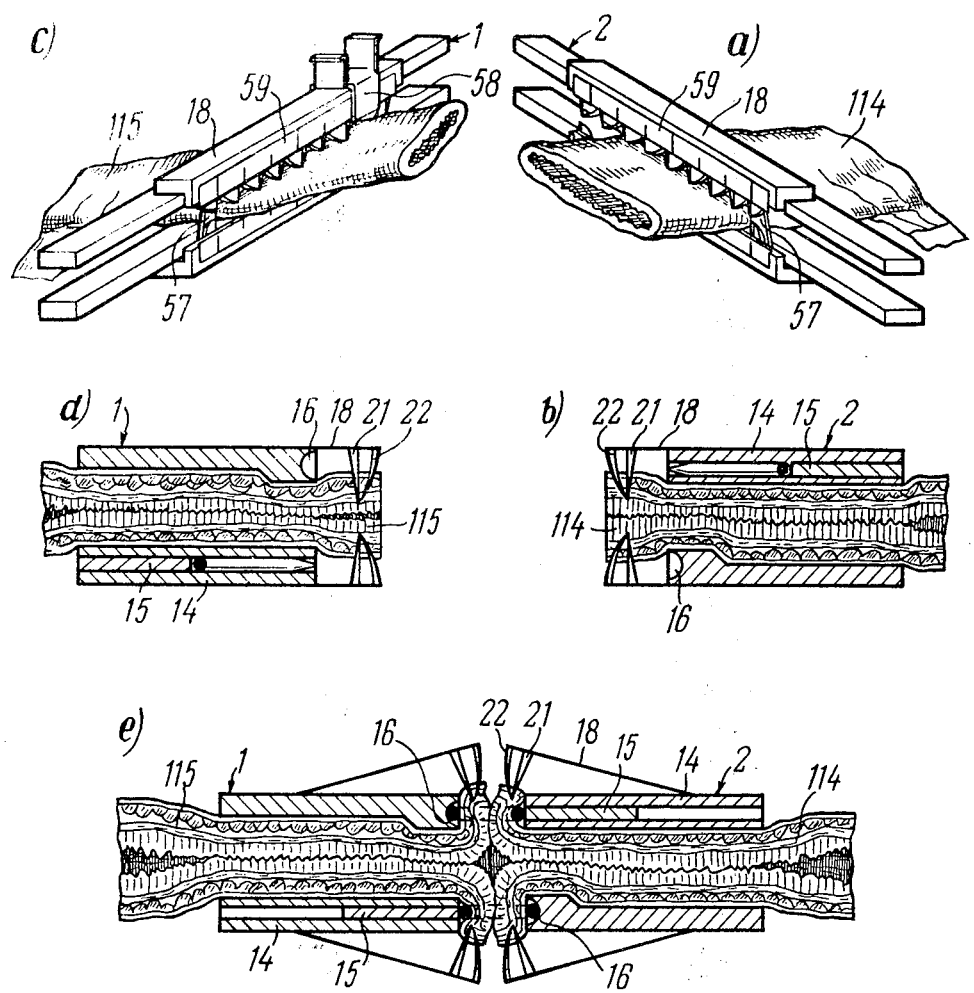
FIG. 32 a, b, c, d and e schematically represent the main stages of surgical procedure involving organ suturing in the end-to-end method by use of the instrument in accordance with the invention.

By simultaneously moving until abutment the handles 91 (FIG. 5) of the plates 84 of both jaws of the clamp 2, the movable plates 20 with the curved teeth 22 (FIG. 5) are moved, providing for the grasping and fixing of the walls of the clinched organ and for the release of the cases 18 (FIG. 3). Then the organ portion to be excised is cut off with a scalpel along the front surface of the cases 18 (FIG. 32b).

The movable stop 58 is positioned by the scales 59 of the clamp 1 (FIG. 32c) in accordance with the size of the semiperimeter of the clinched organ determined by the position of the second portion 115 to be stitched (FIG. 32c) with respect to the graduation notches on the scales 59 (FIG. 32a) of the clamp 2. The organ to be stitched with the smaller semiperimeter in cross section is positioned in an oblique fashion between the movable stop 58 and the stationary stop 57 of the clamp 1. After the organ has been clinched, the organ walls are fixed, the movable stop 58 is removed, and the organ portion to be excised (FIG. 32d) is cut off in the same way as has been described for the clamp 2.

Then the two clamps 1 and 2 are joined which is achieved by aligning the axle and the opening of the hinge 9 (FIG. 1) disposed on the lugs 11 and 12 of the clamps 1 and 2, approximating the jaws of the clamps 1 and 2 so that the forks 65 secured to the jaws of the clamp 2 envelop the jaws of the clamp 1, and turning the hooks 10, thereby rigidly connecting the clamps 1 and 2. This causes the cam projections 28 (FIG. 4) of the cases 18 of the paired jaws of the clamps 1 and 2 to rest against one another, retracting the cases 18 to the backward position to align the fixed walls of the organ portions 114 and 115 to be stitched together, as shown in FIG. 32e and to set them to the position for stitching.

The handles 53 (FIG. 1) of the wedge-shaped drives of the pushers 15 (FIG. 11) are manipulated to force the staples out of the slots of the magazines 14 and effect the stitching of the semiperimeters of the organ walls. The stitching completed, the handles 91 (FIG. 1) are drawn back until abutment against the stop of the plate 84, thereby retracting the curved teeth 22 (FIG. 17) of the plates 20 from the straight teeth 21 of the plates 19 and releasing the organ walls. The hooks 10 are set to the initial position. The springs 67 (FIG. 3) are pressed against the handles 71, forcing the upper and lower jaws of the clamps 1 and 2 apart, the free end 70 of the spring 67 slipping clear of the stepped recesses 69. Then the lower pair of jaws of the clamps 1 and 2 is withdrawn from under the stitched organ.

Figure 34:
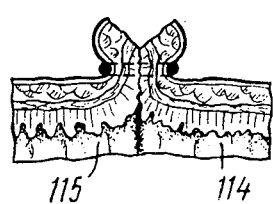
FIG. 34 is a cross sectional view of a suture placed on tubular organs by means of the instrument in accordance with the invention.
Figure 33:
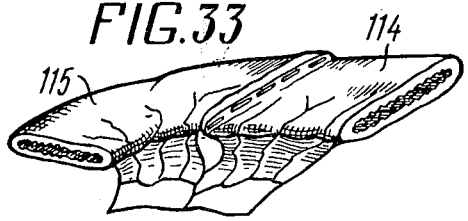
FIG. 33 is an illustration of the organs stitched in the end-to-end method by use of the instrument in accordance with the invention.

The organs stitched with the proposed surgical instrument in the end-to-end method are shown in FIG. 33; the cross sectional view of a typical suture is shown in FIG. 34.

Figure 35:
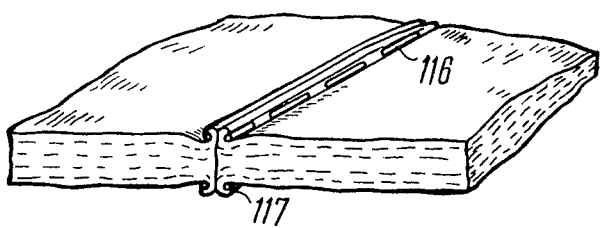
FIG. 35 illustrates a suture placed by means of the instrument in accordance with the invention on solid non-tubular organs.

Stitching of solid (non-hollow) organs requires absolutely the same manipulations of the proposed instrument as have been described for the case of applying anastomoses to hollow organs in the end-to-end method. Solid organs are butt-stitched (FIG. 35). Rows of sutures 116 and 117 are placed on both sides of the walls of the stitched organs.

Figure 36:
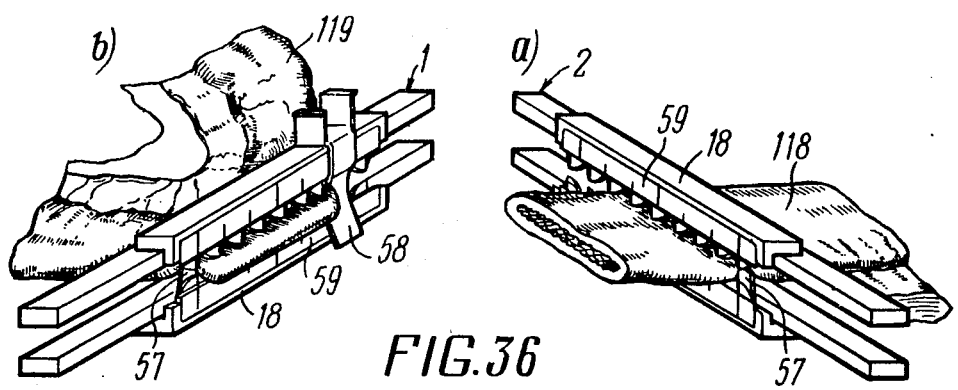
FIG. 36 a and b schematically represent the operation of the instrument in accordance with the invention at the instant of clinching organs while performing stitching in the end-to-side method.
Figure 37:
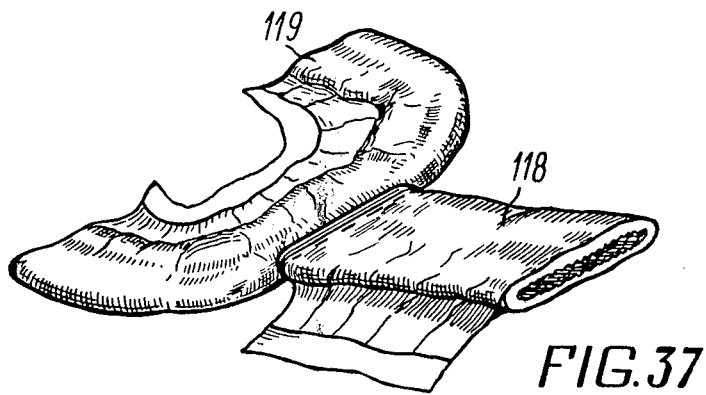
FIG. 37 illustrates organs stitched in the end-to-side method by means of the instrument in accordance with the invention.

When stitching organs in the end-to-side method, the walls of an organ 118 (FIG. 36a) stitched to end are first clinched and fixed, after which the walls of an organ 119 (FIG. 36b) stitched to side are clinched and fixed. The sequence of manipulations and the operation of the instrument are absolutely the same as in the end-to-end stitching operation described hereinabove. The portion of the organ 118 (FIG. 36a) to be exised is cut off, stitching is effected, and the instrument is withdrawn from the surgical wound to reveal the end-to-side suture shown in FIG. 37.

While stitching in the side-to-side method or in any other method, if the semiperimeter of the organ connection, e.g. the lumen of the hollow organs stitched, is preset, the movable stops 58 (FIG. 38a and b) are positioned by the scale 59 of both clamps an equal distance from the stationary stops 57 in accordance with the preset size of the lumen. Then portions of the organs 120 and 121 to be stitched are clinched between the stationary stops 57 and the movable stops 58 of both the clamps. The subsequent operation of the instrument and all manipulations therewith are analogous to those used while applying anastomoses in the end-to-end method. The view of the side-to-side suture obtained in shown in FIG. 39.

The operation of the surgical instrument for stitching organs with the aid of metal staples in accordance with the invention using the second embodiment of the means 13' (FIG. 19 and 20) for grasping and fixing the walls of the organs being stitched is similar to the operation of the proposed instrument incorporating the first embodiment of the means 13 (FIGS. 1 and 2). Among other things, absolutely identical manipulations are involved in the mutual alignment of the organs being stitched in a longitudinal direction relative to the clamp jaws while stitching organs in the end-to-end, end-to-side and side-to-side methods, as well as in the closing of the clamps and in the stitching operation proper.

The differences are as follows. As the organ portions to be stitched are clinched between the jaws of each clamp 1 and 2, the toothed plates 92 (FIG. 25) of the cases 93 crimp the organ walls. The needles 96 (FIG. 26) alternately enter the holes 95 in the toothed plates 92 of the cases 93 of each clamp jaw, dot-piercing the opposite walls of the clinched organ. The lock means 111 (FIG. 20), which serve to fix the cases 93 in their forward position, are moved until abutment, releasing the cases 93. After the clamps (FIG. 19) have been joined and the organs stitched, the needles 96 with the handles 97 are withdrawn from the instrument, the hooks 10 are set to their initial position, and, by actuating the free ends 107 of the spring catches 104, the clamp jaws are driven apart, following which the instrument is withdrawn from the surgical wound.

What is claimed is:

1. A surgical instrument for stitching organs with the aid of metal staples in the end-to-end, end-to-side and side-to-side methods, with the working part of the instrument being disposed exteriorly of the organs being stitched, comprising: two clamps; two jaws of each of said clamps for fixing the organs being stitched therebetween, said clamps being pivotally interconnected at one end so that, with the clamps joined, the joint line of said jaws of each of said clamps is perpendicular to the joint line of said clamps; two magazines with slots for staples, each of said magazines being mounted on one of said jaws of each of said clamps; pushers for forcing said staples out of said slots of said magazines; two dies with recesses for bending the staples, each of said dies being disposed on one of said clamp jaws so that said magazines and dies cooperating in the course of stitching are disposed on the jaws of different clamps; a device for mutually aligning the organs to be stitched in a longitudinal direction with respect to said jaws; a means for grasping and fixing the walls of the organs being stitched; four cases of said means mounted on said jaws, one of said cases being secured to each of the jaws; toothed plates secured to said cases and arranged along said jaws; guides formed in said jaws and securing said cases thereto so as to provide for a limited degree of movability of each of said cases in a plane perpendicular to the joint line of said jaws as well as to the joint line of said clamps, such that each of said cases may be set to either one of two extreme positions, a forward position corresponding to the instant of clinching and grasping the walls of the organs being stitched in which the tips of the teeth of said toothed plates are disposed between the butt surfaces of said jaws of said clamps and a certain distance in front of the butt surfaces of the set-apart clamps, and a backward position corresponding to the instant of organ stitching with said clamps joined in which the tips of the teeth of said toothed plates are disposed a certain distance from the butt surfaces of said clamp jaws and approximately in the planes of the butt surfaces of said clamps.

2. The surgical instrument as set forth in claim 1, in which said cases are provided with pins, and each of said jaws is formed to have closed through slots with inclined portions, said closed through slots defining said guides and cooperating with said pins, so that, as said cases move from one of said extreme positions to the other, said cases simultaneously turn in a plane perpendicular to the butt surfaces of said jaws of each of said clamps as well as to the butt surfaces of the clamps.

3. The surgical instrument as set forth in claim 2, in which there are cam projections provided on each of said cases on the side of said joint line of said clamps, and said cam projections on said cases of the opposite clamps cooperate one with another so that, as said clamps are closed to the position for stitching, said cases are simultaneously transferred from said forward positions to said backward positions.

4. The surgical instrument as set forth in claim 3, in which the shape and layout of said cam projections on said cases are so selected that at each instant of interaction of said cam projections disposed on said opposite cases caused by the closing of said clamps, the forces exerted on these cases are directed eccentrically with respect to the axes of said pins in order to ensure that said cases being moved from said forward positions to said backward positions are simultaneously turned in a required direction.

5. The surgical instrument as set forth in claim 1, further comprising: longitudinal through slots formed in the magazines perpendicular to said slots for the staples; drives for said pushers comprising plates secured to said jaws so as to be able to move lengthwise within said through slots of said magazines and wedge-shaped chamfers defined on the ends of said plates facing said pushers and cooperating with the plates to assist in forcing said staples out of said magazines.

6. The surgical instrument as set forth in claim 5, further comprising: transverse external projections provided on said magazines; transverse recesses formed in said jaws whereon said magazines are mounted cooperating with said projections, thereby enabling said magazines to be mounted and removed; and fixing plates mounted on said jaws for pressing said magazines against said jaws.

7. The surgical instrument as set forth in claim 5, further comprising: handles of said pusher drives; springy sections of these handles; projections formed on said jaws cooperating with said springy sections of said handles and functioning as means for fixing said pusher drives in the initial positions thereof.

8. The surgical instrument as set forth in claim 5, further comprising detachable plates for securing said pusher drives to said jaws.

9. The surgical instrument as set forth in claim 1, further comprising: a split hinge latch interconnecting said clamps at one end; and means for fixing said clamps with respect to each other and providing a required clearance therebetween, said means being provided at the other end of said clamps.

10. The surgical instrument as set forth in claim 1, in which said device for mutually aligning the organs to be stitched in a longitudinal direction with respect to the jaws comprises: stationary stops secured to one of said jaws of each of the clamps and disposed opposite one another, said stationary stops serving to delimit the edges of the semiperimeters of the organs to be stitched clinched between said jaws on one side; and movable stops serving to delimit the edges of the semiperimeters of the organs to be stitched on the other side.

11. The surgical instrument as set forth in claim 10, in which said movable stops are made detachable.

12. The surgical instrument as set forth in claim 1, in which said device for mutually aligning the organs to be stitched in a longitudinal direction with respect to said jaws comprises: stationary stops secured to said cases of said means for grasping and fixing the walls of the organ being stitched disposed on one of said jaws of each of said clamps, arranged opposite one another and serving to delimit the edges of the semiperimeters of the organs being stitched clinched between said jaws on one side; movable stops disposed on said cases of said means for grasping and fixing the walls of the organ being stitched which serve to delimit the edges of the semiperimeters of the organs being stitched on the other side; and graduated scales disposed on said cases.

13. The surgical instrument as set forth in claim 1, further comprising: a lock means for fixing the clearance between said jaws while clinching the organ to be stitched comprising an irregularly shaped lath spring secured with one end thereof to one of said clamp jaws and stepped recesses formed in the other one of said jaws of that same clamp and cooperating with the other end of said spring by way of one of said recesses, the particular recess depending on the wall thickness of the organ being clinched.

14. The surgical instrument as set forth in claim 13, in which said spring protrudes beyond said jaw with said stepped recesses, and in which a handle is provided on said jaw next to said protruding end of said spring so that, with said handle and said spring pressed together, the spring becomes disengaged from said stepped recess.

15. A surgical instrument for stitching organs with the aid of metal staples comprising: two clamps; two jaws of each of said clamps for fixing therebetween one of the organs being stitched; a split hinge latch interconnecting said clamps in such a way that, with said clamps closed, the joint line of said jaws of each of said clamps is perpendicular to the joint line of said clamps; two magazines with slots for staples, each of said magazines being mounted on one of said jaws of each of said clamps; pushers for forcing said staples out of said slots of the magazines which are mounted on said jaws; two dies with recesses for bending the staples, each of said dies being disposed on one of said clamp jaws so that said magazines and dies cooperating in the course of stitching are disposed on the jaws of different clamps; a device for mutually aligning the organs to be stitched in a longitudinal direction with respect to said jaws; a means for grasping and fixing the walls of the organs being stitched; four cases of said means mounted on said jaws, one of said cases being secured to each of the jaws; toothed plates built into said toothed cases, each of said cases mounting two of said toothed plates arranged along said jaws and adjoining each other by way of the lateral surfaces thereof, and one of said plates is rigidly coupled with said case, whereas the other of said plates is so mounted as to be able to slide along said fixed plate; teeth of said plates formed as fixing needles disposed at equal spacings on the surfaces of the longitudinal edges of both of said plates, said fixing needles of one of said plates formed to be straight and approximately perpendicular to said surface of the longitudinal edge of the plate, whereas said fixing needles of the other plate are curved in one direction opposite to the supposed direction of withdrawal of the instrument from the surgery wound and adjoin with the tips thereof the tips of said straight fixing needles, defining closed contours; guides formed in said jaws and enabling said cases to be mounted thereon with a limited degree of movability of each of said cases in a plane perpendicular to the joint line of said jaws and to the joint line of said clamps, such that each of said cases may be set to either one of two extreme positions, a forward position corresponding to the instant of clinching and grasping the walls of the organs being stitched in which the tips of said teeth of said toothed plates lie between the butt surfaces of said jaws of said clamps and a certain distance in front of the butt surfaces of the set-apart clamps, and a backward position corresponding to the instant of organ stitching with said clamps closed in which the tips of said teeth lie a certain distance from the butt surfaces of said clamp jaws and approxiamately in the planes of the butt surfaces of said clamps.

16. The surgical instrument as set forth in claim 15, in which said toothed plates are detachably mounted on said cases.

17. The surgical instrument as set forth in claim 15, comprising: a locking means preventing any possibility of organ stitching if the organ walls are unfixed, which simultaneously functions as the drive of said movable toothed plate; a plate of said locking means disposed along said jaw and movable therealong; a dog of said plate cooperating with said movable toothed plate; stops of said plate cooperating with said cases, the latter protruding, when set to the forward positions thereof, beyond the butt surfaces of said clamps a distance exceeding half the clearance between the butt surfaces of the closed clamps, so that, with said plate set to one of the extreme positions corresponding to the initial position of said movable toothed plate prior to grasping the walls of the organ being stitched; said stops of said plate cooperate with said case, preventing same from moving to the backward position thereof and thereby preventing said clamps from being closed for stitching, whereas, with said plate set to the other extreme position thereof, said movable toothed plate is set to the position for grasping the walls of the organ being stitched with said fixing needles, said stops of said plate being disengaged from said case, enabling same to move to the backward extreme position thereof and thereby enabling the manipulations of clamp closing and stitching to be effected.

18. The surgical instrument as set forth in claim 15, in which said cases are provided with pins, and each of said jaws has closed through slots with inclined portions serving as said guides and cooperating with said pins, so that while moving from one of said extreme positions to the other, said cases simultaneously turn in a plane perpendicular to the butt surfaces of said jaws of each of said clamps as well as to the butt surfaces of these clamps.

19. The surgical instrument as set forth in claim 18, in which there are cam projections provided on each of said cases on the side of said joint line of said clamps, and these cam projections on said cases of the opposite clamps come into contact so that, as said clamps are joined, for stitching, said cases are simultaneously moved from said forward positions to said backward positions thereof.

20. The surgical instrument as set forth in claim 19, in which the shape and layout of said cam projections provided on said cases are so selected that at each instant of interaction of said cam projections on said opposite cases as said clamps are being closed, the forces exerted on said cases are directed eccentrically with respect to the axes of said pins in order that said cases being moved from said forward positions to said backward positions thereof may be simultaneously turned in a required direction.

21. The surgical instrument as set forth in claim 15, further comprising: longitudinal through slots formed in the magazines perpendicular to said slots for the staples; drives for said pushers comprising plates mounted on said jaws so as to be able to move within said through slots of said magazines and wedge shaped chamfers formed on the ends of said plates facing said pushers and cooperating therewith to assist in forcing said staples out of said magazines.

22. The surgical instrument as set forth in claim 15, further comprising two forks rigidly secured to the middle portion of said jaws of one clamp and enveloping said jaws of the other clamp, thereby providing for the interconnection of said jaws.

23. A surgical instrument for stitching organs with the aid of metal staples, comprising: two clamps; two jaws of each of said clamps for fixing therebetween one of the organs being stitched; a split hinge latch interconnecting said clamps so that, with the clamps closed, the joint line of said jaws of each of said clamps is perpendicular to the joint line of the clamps; two magazines with slots for staples, each of said magazines being mounted on one of said jaws of each of said clamps; pushers for forcing said staples out of said slots of said magazines, said pushers being mounted on said jaws; two dies with recesses for bending the staples, each of said dies being so disposed on one of said clamp jaws that said magazines and said dies cooperating in the course of stitching are disposed on the jaws of different clamps; a device for mutually aligning the organs being stitched in a longitudinal direction with respect to said jaws; a means for grasping and fixing the walls of the organs being stitched; four cases of said means mounted on said jaws, each of the jaws carrying one of said cases; toothed plates built into said cases and oriented along said jaws; teeth of said toothed plates wherein are formed coaxial through holes; needles, each of the needles designed for being run through all of said coaxial through holes of each of said cases; guides formed in said jaws which permit mounting said cases therein so that each of said cases is able to execute a limited motion in a plane perpendicular to the joint line of said jaws and to the joint line of said clamps, such that each of said cases may be set to either one of two extreme positions, a forward position corresponding to the instant of clinching and grasping the walls of the organs being stitched in which the tips of said teeth of said toothed plates lie between the butt surfaces of said jaws of said clamps and a certain distance in front of the butt surfaces of said clamps in the set-apart condition thereof, and a backward position corresponding to the instant of organ stitching in the closed condition of said clamps in which the tips of said teeth lie a certain distance from the butt surfaces of said clamp jaws and approximately in the planes of the butt surfaces of said clamps.

24. The surgical instrument as set forth in claim 23, in which said cases are provided with pins, and in each of said jaws there are formed closed through slots with inclined portions which serve as said guides and cooperate with said pins, so that said cases move from one of said extreme positions thereof to the other one, simultaneously turning in a plane perpendicular to the butt surfaces of said jaws of each of said clamps as well as to the butt surfaces of said clamps.

25. The surgical instrument as set forth in claim 24, in which there are cam projections provided on each of said cases on the side of said joint line of said clamps, and these cam projections on said cases of the opposite clamps cooperate so that, as said clamps are closed to the position for stitching, said cases are simultaneously moved from said forward positions to said backward positions.

26. The surgical instrument as set forth in claim 25, in which the shape and layout of said cam projections provided on said cases are so selected that at each instant of interaction of said cam projections of said opposite cases caused by the closing of said clamps, the forces exerted on said cases are directed eccentrically with respect to the axes of said pins in order that said cases being moved from said forward positions to said backward positions thereof may be simultaneously turned in a required direction.

27. The surgical instrument as set forth in claim 23, in which each of said clamps is provided with a spring catch mounted on the ends of the jaws of said clamp, said spring catch serving as a lock means fixing the clearance between said jaws as one end of the organ being stitched is clinched therebetween.

* * * * *